US007601826B2

(12) United States Patent
Nakamura et al.

(10) Patent No.: US 7,601,826 B2
(45) Date of Patent: Oct. 13, 2009

(54) GENES AND POLYPEPTIDES RELATING TO HUMAN PANCREATIC CANCERS

(75) Inventors: Yusuke Nakamura, Yokohama (JP); Toyomasa Katagiri, Shinagawa-ku (JP)

(73) Assignee: Oncotherapy Science, Inc., Kanagawa (JP)

( * ) Notice: Subject to any disclaimer, the term of this patent is extended or adjusted under 35 U.S.C. 154(b) by 397 days.

(21) Appl. No.: 10/529,592

(22) PCT Filed: Sep. 12, 2003

(86) PCT No.: PCT/JP03/11713

§ 371 (c)(1), (2), (4) Date: Mar. 24, 2006

(87) PCT Pub. No.: WO2004/031411

PCT Pub. Date: Apr. 15, 2004

(65) Prior Publication Data

US 2006/0270619 A1    Nov. 30, 2006

Related U.S. Application Data

(60) Provisional application No. 60/414,872, filed on Sep. 30, 2002, provisional application No. 60/450,889, filed on Feb. 28, 2003.

(51) Int. Cl.
*C07H 21/00* (2006.01)
*C12N 15/00* (2006.01)
*C12N 5/00* (2006.01)

(52) U.S. Cl. .................. 536/23.5; 536/23.1; 435/320.1; 435/325

(58) Field of Classification Search .................. None
See application file for complete search history.

(56) References Cited

U.S. PATENT DOCUMENTS

| 6,429,302 B1 | 8/2002 | Kennedy |
| 2005/0260639 A1 | 11/2005 | Nakamura et al. |
| 2006/0024692 A1 | 2/2006 | Nakamura et al. |

FOREIGN PATENT DOCUMENTS

| WO | WO 98/53319 A2 | 11/1998 |
| WO | WO 98/53319 A3 | 11/1998 |
| WO | WO 99/31274 A2 | 6/1999 |
| WO | WO 99/31274 A3 | 6/1999 |
| WO | WO 99/67386 A2 | 12/1999 |
| WO | WO 99/67386 A3 | 12/1999 |
| WO | WO 00/55350 A1 | 9/2000 |
| WO | WO 01/55314 A2 * | 8/2001 |
| WO | WO 01/55314 A3 | 8/2001 |
| WO | WO 01/64835 A2 | 9/2001 |
| WO | WO 01/94629 A2 | 12/2001 |
| WO | WO 01/94629 A3 | 12/2001 |
| WO | WO 02/29103 A2 | 4/2002 |
| WO | WO 02/29103 A3 | 4/2002 |
| WO | WO 02/068579 A2 | 9/2002 |
| WO | WO 02/068579 A3 | 9/2002 |
| WO | WO 03/054152 A2 | 7/2003 |
| WO | WO 2004/031410 A2 | 4/2004 |
| WO | WO 2004/031410 A3 | 4/2004 |

OTHER PUBLICATIONS

Zips et al. (2005, In Vivo, 19:1-7).*
Stein et al (Cancer Research, Apr. 2004, 64:2805-2816).*
Drexler et al (Leukemia and Lymphoma, 1993, 9:1-25).*
Zellner et al (Clin. Can. Res., 1998, 4:1797-17802).*
Slamon et al, (Cancer Cells, 1989, 7:371-384).*
NCBI Sequence Viewer for BQ71560, p. 1-2.*
"Revision History for BQ71560", p. 1.*
NCBI Sequence Viewer for BQ672221, p. 1-2.*
"Revision History for BQ672221", p. 1.*
NCBI Sequence Viewer for BI914593, p. 1-2.*
"Revision History for BI914593", p. 1.*
Ausubel et al, Current Protocols in molecular Biology, 1995, 3rd edition, Wiley & Sons, NY, Section9, p. 9-1 to 9-14).*
Sequence Listing; UniProtKB Accession No. Q96GX8; Dec. 1, 2001.
Database EMBL Nucleotide Sequences [Online], "Agencourt_8303632 NIH_MGC_102 Homo sapiens cDNA clone Image:6274816 5', mRNA sequence," Retrieved from www.ebi.org, Database Accession No. BQ672221 (Aug. 12, 2002).
Database EMBL Nucleotide Sequences [Online], "Agencourt_10154878 NIH_MGC_101 Homo sapiens cDNA clone Image:6536921 5', mRNA sequence," Retrieved from www. ebi.org, Database Accession No. BU527159 (Sep. 16, 2002).
Smith, J.P., et al., "Antisense oligonucleotides to gastrin inhibit growth of human pancreatic cancer," *Cancer Letters*, vol. 135(1), pp. 107-112 (Jan. 8, 1999).
Crnogorac-Jurcevic, Tatjana et al., "Gene expression profiles of pancreatic cancer and stromal desmoplasia"; *Oncogene* 20:7437-7446 (2001).
Crnogorac-Jurcevic, Tatjana et al.; "Expression profiling of microdissected pancreatic adenocarcinomas"; *Oncogene* 21:4587-4594 (2002).
Gress, T.M. et al.; "A pancreatic cancer-specific expression profile"; *Oncogene* 13:1819-1830 (1996).
Han, Haiyong et al.; "Identification of differentially expressed genes in pancreatic cancer cells using cDNA microarray"; *Cancer Research* 62:2890-2896 (May 15, 2002).
Iacobuzio-Donahue, Christine A. et al.; "Discovery of novel tumor markers of pancreatic cancer using global gene expression technology"; *Am. J. Pathol.* 160:1239-1249 (2002).

(Continued)

Primary Examiner—Laura B Goddard
(74) Attorney, Agent, or Firm—Townsend and Townsend and Crew LLP

(57) ABSTRACT

The present application provides novel human genes C1958V1 or C1958V2 whose expression is markedly elevated in pancreatic cancers compared to corresponding non-cancerous tissues. The genes and polypeptides encoded by the genes can be used, for example, in the diagnosis of pancreatic cancer, and as target molecules for developing drugs against the disease.

5 Claims, 6 Drawing Sheets

OTHER PUBLICATIONS

Jordan, Mary Ann and Leslie Wilson; "Microtubules and actin filaments: dynamic targets for cancer chemotherapy"; *Current Opinion in Cell Biology* 10:123-130 (1998).

Nakamura, Toru et al.; "Genome-wide cDNA microarray analysis of gene-expression profiles of pancreatic cancer using cancer cells and normal ductal epithelial cells purely selected by laser microdissection"; *Proceedings of the American Associate for Cancer Research* 44(2nd ed):1205, Abstract #6036 (Jul. 2003).

Nakamura, Toru et al.; "Isolation and characterization of a novel gene as diagnostic and therapeutic target for pancreatic cancer"; *Cancer Science* 94(Suppl):483-484, Abstract #3420-PA (2003) [Proceedings of the 62nd Annual Meeting of the Japanese Cancer Association; Nagoya, Japan; Sep. 25-27, 2003].

Ryu, Byungwoo et al.; "Relationships and differentially expressed genes among pancreatic cancers examined by large-scale serial analysis of gene expression"; *Cancer Research* 62:819-826 (Feb. 1, 2002).

Silverman, Jeffrey A. et al.; "Expression of c-*myc*, c-*raf*-1, and c-Ki-*ras* in azaserine-induced pancreatic carcinomas and growing pancreas in rats"; *Molecular Carcinogenesis* 3:379-386 (1990).

Zhang, Lin et al.; "Gene expression profiles in normal and cancer cells"; *Science* 276:1268-1272 (May 23, 1997).

Database; Biosis Accession No. PREV199191074872; "Expression of c-myc, c-raf-1, and c-Ki-ras in azaserine-induced pancreatic carcinomas and growing pancreas in rats"; 1990.

* cited by examiner a b (a)

(b)

Fig. 5-1
a
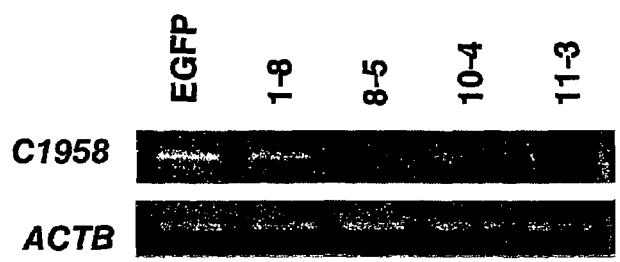
b
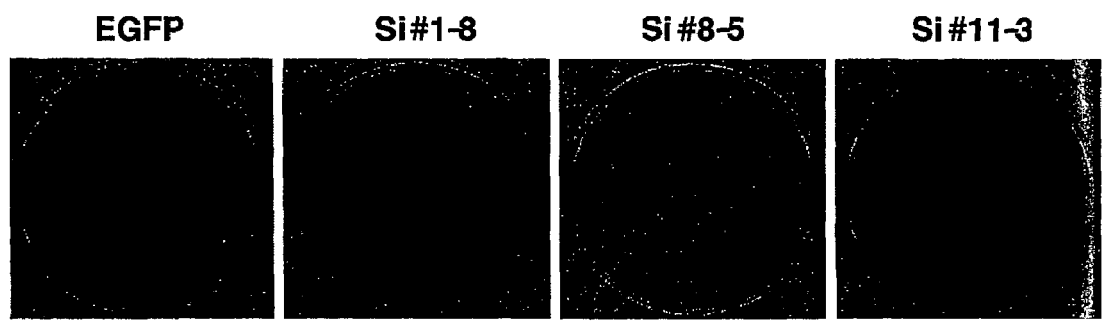
c
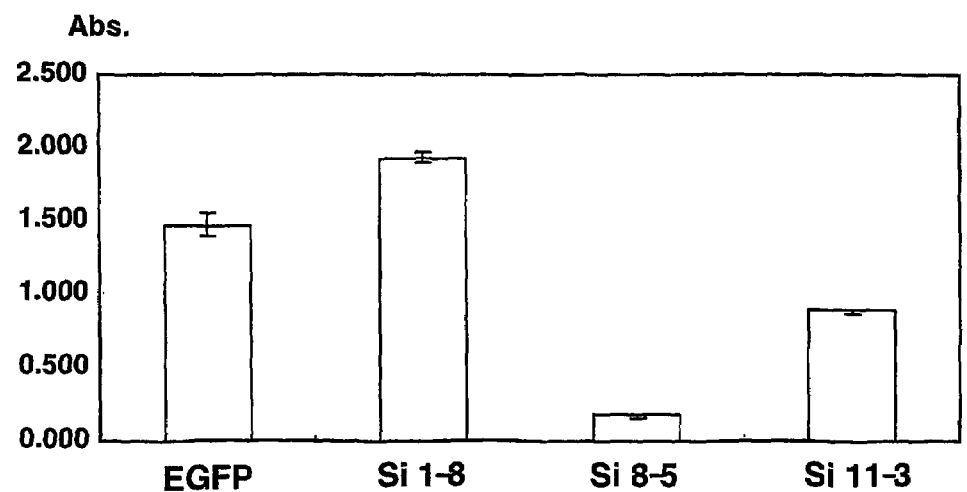

d e

SEQUENCE LISTING

<160> NUMBER OF SEQ ID NOS: 28

<210> SEQ ID NO 1
<211> LENGTH: 881
<212> TYPE: DNA
<213> ORGANISM: Homo sapiens
<220> FEATURE:
<221> NAME/KEY: CDS
<222> LOCATION: (163)...(390)

<400> SEQUENCE: 1

```
gggccatgac ccccgctgct ctgtcttgca ggctcgtcgc cgcggccccc cgagcccgac      60
cgccgccgcc accaccacca gcgcccgggc gggcctcgcg cgcctcgggc gcggctccgc     120
agtgagccca ccaagaagga agcggcctgc agaggtgccg ac atg ggg ctt aag        174
                                               Met Gly Leu Lys
                                                 1 atg tcc tgc ctg aaa ggc ttt caa atg tgt gtc agc agc agc agc agc       222
Met Ser Cys Leu Lys Gly Phe Gln Met Cys Val Ser Ser Ser Ser Ser
  5                  10                  15                  20 agc cac gac gag gcc ccc gtc ctg aac gac aag cac ctg gac gtg ccc       270
Ser His Asp Glu Ala Pro Val Leu Asn Asp Lys His Leu Asp Val Pro
                 25                  30                  35 gac atc atc atc acg ccc ccc acc ccc acg ggc atg atg ctg ccg agg       318
Asp Ile Ile Ile Thr Pro Pro Thr Pro Thr Gly Met Met Leu Pro Arg
         40                  45                  50 gac ttg ggg agc aca gtc tgg ctg gat gag aca ggg tcg tgc cca gat       366
Asp Leu Gly Ser Thr Val Trp Leu Asp Glu Thr Gly Ser Cys Pro Asp
     55                  60                  65 gat gga gaa atc gac cca gaa gcc tgaggaggtg tcctgggttt ggctggctgg      420
Asp Gly Glu Ile Asp Pro Glu Ala
         70                  75 ctcctgctcc agcggcccgg cttcaggtgt ccggggcgt ggctgcctgg agcaggtgtg      480
ctgaataccc tggatgggaa ctgagcgaac ccgggcctcc gctcagagag acgtggcagg     540
accagcgagg aatccagcct gtccacttcc agaacagtgt tcccaggcc ccgctgagtg      600 gaccggacct ctgacaccta caggttcttg ctgactccgg cctggtgaaa gggagcgcca     660
tggtcctggc tgttggggtc ccaggggagag gctctcttct ggacaaacac accctcccag    720
cccccagggc tgtgcaaaca catgcccctg ccataagcac caacaagaac ttcttgcagg     780
tggagtggct gttttttata agttgtttta cagatacgga aacagtccaa aatgggattt     840
ataatttctt ttttgcatta taaataaaga tcctctgtaa c                         881
```

<210> SEQ ID NO 2
<211> LENGTH: 76
<212> TYPE: PRT
<213> ORGANISM: Homo sapiens

<400> SEQUENCE: 2

```
Met Gly Leu Lys Met Ser Cys Leu Lys Gly Phe Gln Met Cys Val Ser
  1               5                  10                  15

Ser Ser Ser Ser Ser His Asp Glu Ala Pro Val Leu Asn Asp Lys His
                 20                  25                  30

Leu Asp Val Pro Asp Ile Ile Ile Thr Pro Pro Thr Pro Thr Gly Met
             35                  40                  45

Met Leu Pro Arg Asp Leu Gly Ser Thr Val Trp Leu Asp Glu Thr Gly
         50                  55                  60
```

Ser Cys Pro Asp Asp Gly Glu Ile Asp Pro Glu Ala
65                  70                  75

<210> SEQ ID NO 3
<211> LENGTH: 893
<212> TYPE: DNA
<213> ORGANISM: Homo sapiens
<220> FEATURE:
<221> NAME/KEY: CDS
<222> LOCATION: (197)...(256)

<400> SEQUENCE: 3

```
ccgcgggagg cgcgcggctg cccgagcgcc ggccgggcca tgaccccgc tgctctgtct      60 tgcaggctcg tcgccgcggc ccccgagcc cgaccgccgc cgccaccacc accagcgccc     120
gggcgggcct cgcgcgcctc gggcgcggct ccgcagtgag cccaccaaga aggaagcggc     180
ctgcagaggt gccgac atg ggg ctt aag atg tcc tgc ctg aaa gca gca gca     232
                Met Gly Leu Lys Met Ser Cys Leu Lys Ala Ala Ala
                  1               5                  10 gca gcc acg acg agg ccc ccg tcc tgaacgacaa gcacctggac gtgcccgaca      286
Ala Ala Thr Thr Arg Pro Pro Ser
            15                  20 tcatcatcac gccccccacc cccacgggca tgatgctgcc gagggacttg gggagcacag     346
tctggctgga tgagacaggg tcgtgcccag atgatggaga atcgaccca gaagcctgag     406 gaggtgtcct gggtttggct ggctggctcc tgctccagcg gccggcttc aggtgtccgg      466 gggcgtggct gcctggagca ggtgtgctga ataccctgga tgggaactga gcgaacccgg     526
gcctccgctc agagagacgt ggcaggacca gcgaggaatc cagcctgtcc acttccagaa     586 cagtgttttcc caggccccgc tgagtggacc ggacctctga cacctccagg ttcttgctga     646
ctccggcctg gtgaaaggga gcgccatggt cctggctgtt ggggtcccag ggagaggctc     706
tcttctggac aaacacaccc tcccagcccc cagggctgtg caaacacatg cccctgccat     766
aagcaccaac aagaacttct tgcaggtgga gtggctgttt ttataagtt gttttacaga     826 tacggaaaca gtccaaaatg ggattttataa tttcttttttt gcattataaa taaagatcct     886
ctgtaac                                                               893
```

<210> SEQ ID NO 4
<211> LENGTH: 20
<212> TYPE: PRT
<213> ORGANISM: Homo sapiens

<400> SEQUENCE: 4

Met Gly Leu Lys Met Ser Cys Leu Lys Ala Ala Ala Ala Thr Thr
  1               5                  10                  15

Arg Pro Pro Ser
            20

<210> SEQ ID NO 5
<211> LENGTH: 21
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 5
gtcctgaaag tcaagcacct g                                               21

<210> SEQ ID NO 6

```
<211> LENGTH: 23
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 6
gaagttcttg ttggtgctta tgg                                           23

<210> SEQ ID NO 7
<211> LENGTH: 23
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 7
cttgggtctg taacaaagca ttc                                           23

<210> SEQ ID NO 8
<211> LENGTH: 23
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 8
aaggattatg aggaggttgg tgt                                           23

<210> SEQ ID NO 9
<211> LENGTH: 21
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 9
gtcctgaaag tcaagcacct g                                             21

<210> SEQ ID NO 10
<211> LENGTH: 23
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 10
gaagttcttg ttggtgctta tgg                                           23

<210> SEQ ID NO 11
<211> LENGTH: 30
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 11
ccggaattcg acatggggct taagatgtcc                                    30

<210> SEQ ID NO 12
<211> LENGTH: 30
```

```
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 12
ccgctcgagg gcttctgggt cgatttctcc                                      30

<210> SEQ ID NO 13
<211> LENGTH: 20
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 13
ggggatcagc gtttgagtaa                                                 20

<210> SEQ ID NO 14
<211> LENGTH: 20
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 14
taggccccac ctccttctat                                                 20

<210> SEQ ID NO 15
<211> LENGTH: 30
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 15
tgcggatcca gagcagattg tactgagagt                                      30

<210> SEQ ID NO 16
<211> LENGTH: 29
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 16
ctctatctcg agtgaggcgg aaagaacca                                       29

<210> SEQ ID NO 17
<211> LENGTH: 40
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 17
tttaagcttg aagactattt ttacatcagg ttgttttttct                          40

<210> SEQ ID NO 18
<211> LENGTH: 37
<212> TYPE: DNA
```

<213> ORGANISM: Artificial Sequence
<220> FEATURE:
<223> OTHER INFORMATION: Artificially synthesized primer sequence for
      RT-PCR

<400> SEQUENCE: 18
tttaagcttg aagacacggt gtttcgtcct ttccaca                              37

<210> SEQ ID NO 19
<211> LENGTH: 51
<212> TYPE: DNA
<213> ORGANISM: Artificial Sequence
<220> FEATURE:
<223> OTHER INFORMATION: Artificially synthesized target sequence for
      siRNA

<400> SEQUENCE: 19
caccgaagca gcacgacttc ttcttcaaga gagaagaagt cgtgctgctt c              51

<210> SEQ ID NO 20
<211> LENGTH: 51
<212> TYPE: DNA
<213> ORGANISM: Artificial Sequence
<220> FEATURE:
<223> OTHER INFORMATION: Artificially synthesized target sequence for
      siRNA

<400> SEQUENCE: 20
aaaagaagca gcacgacttc ttctctcttg aagaagaagt cgtgctgctt c              51

<210> SEQ ID NO 21
<211> LENGTH: 21
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 21
gtcctgaaag tcaagcacct g                                              21

<210> SEQ ID NO 22
<211> LENGTH: 23
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 22
gaagttcttg ttggtgctta tgg                                            23

<210> SEQ ID NO 23
<211> LENGTH: 23
<212> TYPE: DNA
<213> ORGANISM: Artificial Sequence
<220> FEATURE:
<223> OTHER INFORMATION: Artificially synthesized primer sequence for
      RT-PCR

<400> SEQUENCE: 23
catccacgaa actaccttca act                                            23

<210> SEQ ID NO 24
<211> LENGTH: 23
<212> TYPE: DNA
<213> ORGANISM: Artificial Sequence

```
<220> FEATURE:
<223> OTHER INFORMATION: Artificially synthesized primer sequence for
      RT-PCR

<400> SEQUENCE: 24
tctccttaga gagaagtggg gtg                                              23

<210> SEQ ID NO 25
<211> LENGTH: 19
<212> TYPE: DNA
<213> ORGANISM: Artificial Sequence
<220> FEATURE:
<223> OTHER INFORMATION: Target sequence for siRNA

<400> SEQUENCE: 25
cgacaagcac ctggacgtg                                                   19

<210> SEQ ID NO 26
<211> LENGTH: 19
<212> TYPE: DNA
<213> ORGANISM: Artificial Sequence
<220> FEATURE:
<223> OTHER INFORMATION: Target sequence for siRNA

<400> SEQUENCE: 26
atgtgtgtca gcagcagca                                                   19

<210> SEQ ID NO 27
<211> LENGTH: 19
<212> TYPE: DNA
<213> ORGANISM: Artificial Sequence
<220> FEATURE:
<223> OTHER INFORMATION: Target sequence for siRNA

<400> SEQUENCE: 27
tccagcctgt ccacttcca                                                   19

<210> SEQ ID NO 28
<211> LENGTH: 19
<212> TYPE: DNA
<213> ORGANISM: Artificial Sequence
<220> FEATURE:
<223> OTHER INFORMATION: Target sequence for siRNA

<400> SEQUENCE: 28
gttgttttac agatacgga                                                   19
```

GENES AND POLYPEPTIDES RELATING TO HUMAN PANCREATIC CANCERS

The present application is related to U.S. Ser. No. 60/414,872, filed Sep. 30, 2002 and U.S. Ser. No. 60/450,889, filed Feb. 28, 2003 which is incorporated herein by reference.

TECHNICAL FIELD

The present invention relates to the field of biological science, more specifically to the field of cancer research. In particular, the present invention relates to novel genes, C1958V1 and C1958V2, involved in the proliferation mechanism of cells, as well as polypeptides encoded by the genes. The genes and polypeptides of the present invention can be used, for example, in the diagnosis of cell proliferative disease, and as target molecules for developing drugs against the disease.

BACKGROUND ART

The mortality among patients with pancreatic cancer is worse than for any other kind of malignant tumor, with a 5-year survival rate only 4% (Greenlee et al., 2001). The poor prognosis of this malignancy reflects both the difficulty of early diagnosis and a generally poor response to current therapies (DiMagno et al., 1999; Greenlee et al., 2001). In particular, no tumor marker is clinically available for detection of this disease at an early and potentially curative stage. Surgical resection is the only possible cure at present, but cases that are surgically resectable at diagnosis account for fewer than 20% of patients with this cancer (DiMagno et al., 1999; Klinkenbijl et al., 1999). Endoscopic ultrasonography (EUS), endoscopic retrograde cholangiopancreography (ERCP) and spiral CT are available to screen individuals at risk for familial pancreatic cancer (Brentnall et al., 1999), but those approaches are not practical in terms of time and cost-effectiveness to screen every asymptomatic individual. Hence, tumor markers that are sensitive and specific for pancreatic cancer must be discovered.

Almost all patients at an advanced stage fail to respond to any treatment. To overcome that situation, some clinical trials have been attempting to establish therapeutic strategies on the basis of molecular technologies. Such trials have involved, for example, an MMP inhibitor, drugs designed to inhibit Ras farnesyltransferase, and antibody-based approaches (Hao and Rowinsky, 2002; Laheru et al., 2001; Rosenberg, 2000). However, so far these experiments have achieved no remarkable effects on this disease.

cDNA microarray technologies have enabled to obtain comprehensive profiles of gene expression in normal and malignant cells, and compare the gene expression in malignant and corresponding normal cells (Okabe et al., Cancer Res 61:2129-37 (2001); Kitahara et al., Cancer Res 61: 3544-9 (2001); Lin et al., Oncogene 21:4120-8 (2002); Hasegawa et al., Cancer Res 62:7012-7 (2002)). This approach enables to disclose the complex nature of cancer cells, and helps to understand the mechanism of carcinogenesis. Identification of genes that are deregulated in tumors can lead to more precise and accurate diagnosis of individual cancers, and to develop novel therapeutic targets (Bienz and Clevers, Cell 103:311-20 (2000)). To disclose mechanisms underlying tumors from a genome-wide point of view, and discover target molecules for diagnosis and development of novel therapeutic drugs, the present inventors have been analyzing the expression profiles of tumor cells using a cDNA microarray of 23040 genes (Okabe et al., Cancer Res 61:2129-37 (2001); Kitahara et al., Cancer Res 61:3544-9 (2001); Lin et al., Oncogene 21:4120-8 (2002); Hasegawa et al., Cancer Res 62:7012-7 (2002)).

Studies designed to reveal mechanisms of carcinogenesis have already facilitated identification of molecular targets for anti-tumor agents. Through analysis of expression profiles of hepatocellular carcinomas (HCC), for example, frequent up-regulation of the VANGL1 gene was detected in tumor cells, and demonstrated that suppressing expression of that gene with antisense-oligonucleotides can significantly decrease growth of HCC cells and induce apoptotic cell death (Yagyu et al., 2002). Furthermore, using the same genome-wide cDNA microarray, several other genes involved in tumorigenesis in the colon, such as AF17 (Lin et al., 2001), AXUD1 (Ishiguro et al., 2001), HELAD1 (Ishiguro et al., 2002), ENC1 (Fujita et al., 2002), and APCDD1 (Takahashi et al., 2002) have been isolated. Expression levels of those genes correlate with activity of the T-cell factor/lymphoid enhancer-binding factor (Tcf-LEF) transcription complex, and are significantly elevated in colon-cancer cells. Furthermore, inhibitors of farnexyltransferase (FTIs) which were originally developed to inhibit the growth-signaling pathway related to Ras, whose activation depends on posttranslational farnesylation, has been effective in treating Ras-dependent tumors in animal models (He et al., Cell 99:335-45 (1999)). Clinical trials on human using a combination or anti-cancer drugs and anti-HER2 monoclonal antibody, trastuzumab, have been conducted to antagonize the proto-oncogene receptor HER2/neu; and have been achieving improved clinical response and overall survival of breast-cancer patients (Lin et al., Cancer Res 61:6345-9 (2001)). A tyrosine kinase inhibitor, STI-571, which selectively inactivates bcr-abl fusion proteins, has been developed to treat chronic myelogenous leukemias wherein constitutive activation of bcr-abl tyrosine kinase plays a crucial role in the transformation of leukocytes. Agents of these kinds are designed to suppress oncogenic activity of specific gene products (Fujita et al., Cancer Res 61:7722-6 (2001)). Therefore, gene products commonly up-regulated in cancerous cells may serve as potential targets for developing novel anti-cancer agents.

It has been demonstrated that CD8+ cytotoxic T lymphocytes (CTLs) recognize epitope peptides derived from tumor-associated antigens (TAAs) presented on MHC Class I molecule, and lyse tumor cells. Since the discovery of MAGE family as the first example of TAAs, many other TAAs have been discovered using immunological approaches (Boon, Int J Cancer 54: 177-80 (1993); Boon and van der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52(1994)). Some of the discovered TAAs are now in the stage of clinical development as targets of immunotherapy. TAAs discovered so far include MAGE (van der Bruggen et al., Science 254: 1643-7 (1991)), gp100 (Kawakami et al., J Exp Med 180: 347-52 (1994)), SART (Shichijo et al., J Exp Med 187: 277-88 (1998)), and NY-ESO-1 (Chen et al., Proc Natl Acad Sci USA 94: 1914-8 (1997)). On the other hand, gene products which had been demonstrated to be specifically overexpressed in tumor cells, have been shown to be recognized as targets inducing cellular immune responses. Such gene products include p53 (Umano et al., Brit J Cancer 84: 1052-7 (2001)), HER2/neu (Tanaka et al., Brit J Cancer 84: 94-9 (2001)), CEA (Nukaya et al., Int J Cancer 80: 92-7 (1999)), and so on.

In spite of significant progress in basic and clinical research concerning TAAs (Rosenbeg et al., Nature Med 4: 321-7 (1998); Mukherji et al., Proc Natl Acad Sci USA 92:

8078-82 (1995); Hu et al., Cancer Res 56: 2479-83 (1996)), only limited number of candidate TAAs are available. TAAs abundantly expressed in cancer cells, and at the same time which expression is restricted to cancer cells would be promising candidates as immunotherapeutic targets. Further, identification of new TAAs inducing potent and specific antitumor immune responses is expected to encourage clinical use of peptide vaccination strategy in various types of cancer (Boon and can der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994); Shichijo et al., J Exp Med 187: 277-88 (1998); Chen et al., Proc Natl Acad Sci USA 94: 1914-8 (1997); Harris, J Natl Cancer Inst 88: 1442-5 (1996); Butterfield et al., Cancer Res 59: 3134-42 (1999); Vissers et al., Cancer Res 59: 5554-9 (1999); van der Burg et al., J Immunol 156: 3308-14 (1996); Tanaka et al., Cancer Res 57: 4465-8 (1997); Fujie et al., Int J Cancer 80: 169-72 (1999); Kikuchi et al., Int J Cancer 81: 459-66 (1999); Oiso et al., Int J Cancer 81: 387-94 (1999)).

It has been repeatedly reported that peptide-stimulated peripheral blood mononuclear cells (PBMCs) from certain healthy donors produce significant levels of IFN-γ in response to the peptide, but rarely exert cytotoxicity against tumor cells in an HLA-A24 or -A0201 restricted manner in $^{51}$Cr-release assays (Kawano et al., Cance Res 60: 3550-8 (2000); Nishizaka et al., Cancer Res 60: 4830-7 (2000); Tamura et al., Jpn J Cancer Res 92: 762-7(2001)). However, both of HLA-A24 and HLA-A0201 are one of the popular HLA alleles in Japanese, as well as Caucasian (Date et al., Tissue Antigens 47: 93-101 (1996); Kondo et al., J Immunol 155: 4307-12 (1995); Kubo et al., J Immunol 152: 3913-24 (1994); Imanishi et al., Proceeding of the eleventh International Hictocompatibility Workshop and Conference Oxford University Press, Oxford, 1065 (1992); Williams et al., Tissue Antigen 49: 129(1997)). Thus, antigenic peptides of cancers presented by these HLAs may be especially useful for the treatment of cancers among Japanese and Caucasian. Further, it is known that the induction of low-affinity CTL in vitro usually results from the use of peptide at a high concentration, generating a high level of specific peptide/MHC complexes on antigen presenting cells (APCs), which will effectively activate these CTL (Alexander-Miller et al., Proc Natl Acad Sci USA 93: 4102-7 (1996)).

SUMMARY OF THE INVENTION

An object of the present invention is to provide novel proteins involved in the proliferation mechanism of pancreatic cancer cells and the genes encoding the proteins, as well as methods for producing and using the same in the diagnosis and treatment of pancreatic cancer.

To disclose the mechanism of pancreatic carcinogenesis and identify novel diagnostic markers and/or drug targets for the treatment of these tumors, the present inventors analyzed the expression profiles of genes in pancreatic carcinogenesis using a genome-wide cDNA microarray containing 23040 genes. From the pharmacological point of view, suppressing oncogenic signals is easier in practice than activating tumor-suppressive effects. Thus, the present inventors searched for genes that are up-regulated during pancreatic carcinogenesis.

Among these up-regulated genes, a novel human gene, C1958, that was significantly up-regulated in 70% of the pancreatic cancer cases which were able to obtain expression data was identified. Through the screening of cDNA library which made of pancreatic cancer cell line Capan-1, the present inventors found three variant transcripts. Among the three variants, C1958V1 encoded with 76 amino-acid protein and C1958V2 encoded with 20 amino-acid protein were specifically expressed in pancreatic cancer cell lines by Northern blot analysis. Moreover, immunohistochemical staining shows this C1958V1 product localized to the cytoplasmic apparatus in COS7 cells. In addition, C1958V1 translated to gene products of a larger size than that predicted by Western blot analysis, suggesting this might be generated by post-translational modification.

Furthermore, reduction of C1958V1 or C1958V2 expression by transfection of their specific antisense S-oligonucleotides or small interfering RNAs inhibited the growth of pancreatic cancer cells. Many anticancer drugs, such as inhibitors of DNA and/or RNA synthesis, metabolic suppressors, and DNA intercalators, are not only toxic to cancer cells but also for normally growing cells. However, agents suppressing the expression of C1958V1 or C1958V2 may not adversely affect other organs due to the fact that normal expression of the gene is mainly observed in the placenta and weakly observed in the liver, thyroid, trachea or bone marrow, and thus may be of great importance for treating cancer.

Thus, the present invention provides isolated novel genes, C1958V1 and C1958V2, which are candidates as diagnostic markers for cancer as well as promising potential targets for developing new strategies for diagnosis and effective anti-cancer agents. Further, the present invention provides polypeptides encoded by these genes, as well as the production and the use of the same. More specifically, the present invention provides the following:

The present application provides novel human polypeptides, C1958V1 and C1958V2, or a functional equivalent thereof, that promotes cell proliferation and is up-regulated in cell proliferative diseases, such as pancreatic cancers.

In a preferred embodiment, the C1958V1 polypeptide includes a putative 76 amino acid protein with about 59% identity to hypothetical protein [*Rattus norvegicus*] (XP_226536). C1958V1 is encoded by the open reading frame of SEQ ID NO: 1. The C1958V1 polypeptide preferably includes the amino acid sequence set forth in SEQ ID NO: 2. The present application also provides an isolated protein encoded from at least a portion of the C1958V1 polynucleotide sequence, or polynucleotide sequences at least 15%, preferably at least 25%, or more preferably 60%, or more preferably 70% or more preferably 90% complementary to the sequence set forth in SEQ ID NO: 1.

On the other hand, in a preferred embodiment, the C1958V2 polypeptide includes a putative 20 amino acid protein encoded by the open reading frame of SEQ ID NO: 3. The C1958V2 polypeptide preferably includes the amino acid sequence set forth in SEQ ID NO: 4. The present application also provides an isolated protein encoded from at least a portion of the C1958V2 polynucleotide sequence, or polynucleotide sequences at least 15%, preferably at least 25%, or more preferably 60%, or more preferably 70% or more preferably 90% complementary to the sequence set forth in SEQ ID NO: 3.

The present invention further provides novel human genes, C1958V1 and C1958V2, whose expressions are markedly elevated in a great majority of pancreatic cancers as compared to corresponding normal pancreatic cells. The isolated C1958V1 gene includes a polynucleotide sequence as described in SEQ ID NO: 1. In particular, the C1958V1 cDNA includes 881 nucleotides that contain an open reading frame of 228 nucleotides (SEQ ID NO: 1). The present invention further encompasses polynucleotides which hybridize to and which are at least 15%, preferably at least 25%, or more preferably 60%, or more preferably 70% or more preferably 90% complementary to the polynucleotide sequence set forth in SEQ ID NO: 1, to the extent that they encode a C1958V1 protein or a functional equivalent thereof. Examples of such polynucleotides are degenerates and allelic mutants of SEQ ID NO: 1. On the other hand, the isolated C1958V2 gene includes a polynucleotide sequence as described in SEQ ID NO: 3. In particular, the C1958V2 cDNA includes 893 nucleotides that contain an open reading frame of 60 nucleotides (SEQ ID NO: 3). The present invention further encompasses polynucleotides which hybridize to and which are at least 15%, preferably at least 25%, or more preferably 60%, or more preferably 70% or more preferably 90% complementary to the polynucleotide sequence set forth in SEQ ID NO: 3, to the extent that they encode a C1958V2 protein or a functional equivalent thereof. Examples of such polynucleotides are degenerates and allelic mutants of SEQ ID NO: 3.

As used herein, an isolated gene is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide.

Accordingly, in one aspect, the invention provides an isolated polynucleotide that encodes a polypeptide described herein or a fragment thereof. Preferably, the isolated polypeptide includes a nucleotide sequence that is at least 60% identical to the nucleotide sequence shown in SEQ ID NO: 1 or 3. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO: 1 or 3. In the case of an isolated polynucleotide which is longer than or equivalent in length to the reference sequence, e.g., SEQ ID NO: 1 or 3, the comparison is made with the full length of the reference sequence. Where the isolated polynucleotide is shorter than the reference sequence, e.g., shorter than SEQ ID NO: 1 or 3, the comparison is made to segment of the reference sequence of the same length (excluding any loop required by the homology calculation).

The present invention also provides a method of producing a protein by transfecting or transforming a host cell with a polynucleotide sequence encoding the C1958V1 or C1958V2 protein, and expressing the polynucleotide sequence. In addition, the present invention provides vectors comprising a nucleotide sequence encoding the C1958V1 or C1958V2 protein, and host cells harboring a polynucleotide encoding the C1958V1 or C1958V2 protein. Such vectors and host cells may be used for producing the C1958V1 or C1958V2 protein.

An antibody that recognizes the C1958V1 or C1958V2 protein is also provided by the present application. In part, an antisense polynucleotide (e.g., antisense DNA), ribozyme, and siRNA (small interfering RNA) of the C1958V1 or C1958V2 gene is also provided.

The present invention further provides a method for diagnosis of cell proliferative diseases that includes determining an expression level of the gene in biological sample of specimen, comparing the expression level of C1958V1 or C1958V2 gene with that in normal sample, and defining a high expression level of the C1958V1 or C1958V2 gene in the sample as having a cell proliferative disease such as cancer. The disease diagnosed by the expression level of C1958V1 or C1958V2 is suitably a pancreatic cancer.

Further, a method of screening for a compound for treating a cell proliferative disease is provided. The method includes contacting the C1958V1 or C1958V2 polypeptide with test compounds, and selecting test compounds that bind to the C1958V1 or C1958V2 polypeptide.

The present invention further provides a method of screening for a compound for treating a cell proliferative disease, wherein the method includes contacting the C1958V1 or C1958V2 polypeptide with a test compound, and selecting the test compound that suppresses the expression level or biological activity of the C1958V1 or C1958V2 polypeptide.

The present application also provides a pharmaceutical composition for treating cell proliferative disease, such as cancer. The pharmaceutical composition may be, for example, an anti-cancer agent. The pharmaceutical composition can be described as at least a portion of the antisense S-oligonucleotides or siRNA of the C1958V1 or C1958V2 polynucleotide sequence. A suitable siRNA consists of a set of nucleotides comprising the nucleotide sequences selected from the group of SEQ ID NOs:25,26 or 28 as the target sequences. The siRNA of C1958V1 consisting of a set of nucleotides comprising the nucleotide sequence of SEQ ID NOs:25,26 or 28 as the target sequences may be suitably used to treat pancreatic cancer. The pharmaceutical compositions may be also those comprising the compounds selected by the present methods of screening for compounds for treating cell proliferative diseases.

The course of action of the pharmaceutical composition is desirably to inhibit growth of the cancerous cells. The pharmaceutical composition may be applied to mammals including humans and domesticated mammals.

The present invention further provides methods for treating a cell proliferative disease using the pharmaceutical composition provided by the present invention.

In addition, the present invention provides method for treating or preventing cancer, which method comprises the step of administering the C1958V1 or C1958V2 polypeptide. It is expected that anti tumor immunity be induced by the administration of the C1958V1 or C1958V2 polypeptide. Thus, the present invention also provides method for inducing anti tumor immunity, which method comprises the step of administering the C1958V1 or C1958V2 polypeptide, as well as pharmaceutical composition for treating or preventing cancer comprising the C1958V1 or C1958V2 polypeptide.

It is to be understood that both the foregoing summary of the invention and the following detailed description are of a preferred embodiment, and not restrictive of the invention or other alternate embodiments of the invention.

BRIEF DESCRIPTION OF THE DRAWINGS

FIG. 4 (b) depicts expression of the C1958V1 variant in mammalian cells by Western Blot analysis. Arrows indicate C1958V1 specific bands.

FIG. 5 (a) depicts Semi-quantitative RT-PCR analysis showing suppression of endogenous expression of C1958V1 in pancreatic cancer cell (KLM-1) at 20-day cultures in selective medium containing neomycin after introduction of siRNAs into KLM-1 cells. β-actin (ACTB) was used as an internal control. FIG. 5(b) presents photographs depicting the result of Gimza's staining of KLM-1 cells after the treatment with either psiU6BX-C1958V1 or psiU6BX-EGFP. FIG. 5(c) depicts the result of MTT assay on KLM-1 cells transfected with either psiU6BX-C1958V1 or psiU6BX-EGFP. FIG. 5(d) presents photographs depicting the result of Gimza's staining of PK59 cells after the treatment with either psiU6BX-C1958V1 or psiU6BX-EGFP. FIG. 5(e) depicts the result of MTT assay on PK59 cells transfected with either psiU6BX-C1958V1 or psiU6BX-EGFP. These experiments were carried out five times as well.

DETAILED DESCRIPTION OF THE INVENTION

Figure 1:
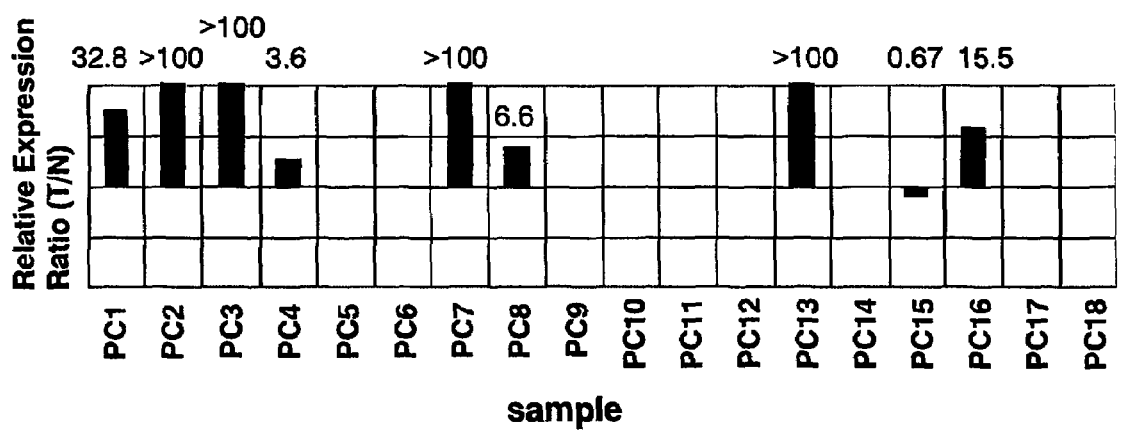
FIG. 1(a) depicts Cy5/Cy3 signal-intensity ratios of C1958 determined by microarray analysis in tumor cells from 18 patients with pancreatic cancer.
FIG. 1(b) depicts semi-quantitative RT-PCR analysis of C1958 expression in tumor cells from pancreatic cancer patients (PC1, PC4, PC5, PC6, PC7, PC8, PC13, PC14, PC15, PC16, PC17, PC18) and pancreatic cancer cell lines (Panc-1, Aspc-1, Miapaca-2, Capan-1 and Capan-2)
Figure 1:
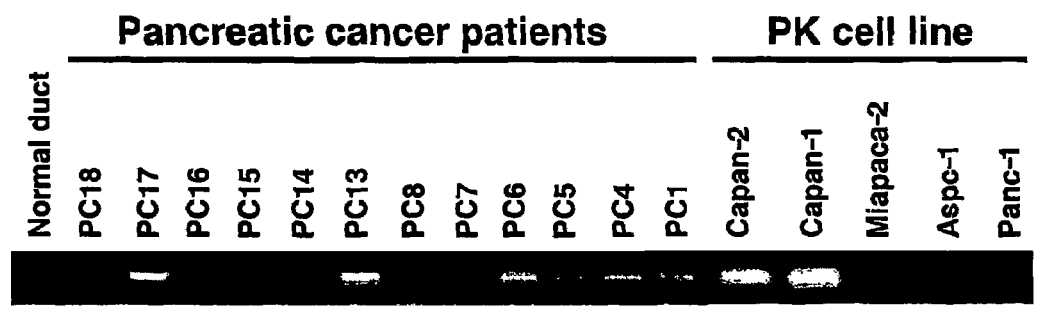

The words "a", "an", and "the" as used herein mean "at least one" unless otherwise specifically indicated.

The present application identifies novel human genes C1958V1 and C1958V2 whose expression is markedly elevated in pancreatic cancer compared to corresponding non-cancerous tissues. The C1958V1 cDNA consists of 881 nucleotides that contain an open reading frame of 228 nucleotides as set forth in SEQ ID NO: 1. The open reading frame encodes a putative 76-amino acid protein. On the other hand, the C1958V2 cDNA consists of 893 nucleotides that contain an open reading frame of 60 nucleotides as set forth in SEQ ID NO: 3. The open reading frame encodes a putative 20-amino acid protein.

Consistently, exogenous expression of C1958V1 or C1958V2 into cells conferred increased cell growth, while suppression of its expression with antisense S-oligonucleotides or small interfering RNA (siRNA) resulted in significant growth-inhibition of cancerous cells. These findings suggest that C1958V1 and C1958V2 render oncogenic activities to cancer cells, and that inhibition of the activity of these proteins could be a promising strategy for the treatment of cancer.

The present invention encompasses novel human gene C1958V1, including a polynucleotide sequence as described in SEQ ID NO: 1, as well as degenerates and mutants thereof, to the extent that they encode a C1958V1 protein, including the amino acid sequence set forth in SEQ ID NO: 2 or its functional equivalent. Examples of polypeptides functionally equivalent to C1958V1 include, for example, homologous proteins of other organisms corresponding to the human C1958V1 protein, as well as mutants of human C1958V1 proteins.

The present invention also encompasses novel human gene C1958V2, including a polynucleotide sequence as described in SEQ ID NO: 3, as well as degenerates and mutants thereof, to the extent that they encode a C1958V2 protein, including the amino acid sequence set forth in SEQ ID NO: 4 or its functional equivalent. Examples of polypeptides functionally equivalent to C1958V2 include, for example, homologous proteins of other organisms corresponding to the human C1958V2 protein, as well as mutants of human C1958V2 proteins.

In the present invention, the term "functionally equivalent" means that the subject polypeptide has the activity to promote cell proliferation like C1958V1 or C1958V2 protein and to confer oncogenic activity to cancer cells. Whether the subject polypeptide has a cell proliferation activity or not can be judged by introducing the DNA encoding the subject polypeptide into a cell expressing the respective polypeptide, and detecting promotion of proliferation of the cells or increase in colony forming activity. Such cells include, for example, NIH3T3 cells, COS7 cells.

Methods for preparing polypeptides functionally equivalent to a given protein are well known by a person skilled in the art and include known methods of introducing mutations into the protein. For example, one skilled in the art can prepare polypeptides functionally equivalent to the human C1958V1 or C1958V2 protein by introducing an appropriate mutation in the amino acid sequence of either of these proteins by site-directed mutagenesis (Hashimoto-Gotoh et al., Gene 152:271-5 (1995); Zoller and Smith, Methods Enzymol 100: 468-500 (1983); Kramer et al., Nucleic Acids Res. 12:9441-9456 (1984); Kramer and Fritz, Methods Enzymol 154: 350-67 (1987); Kunkel, Proc Natl Acad Sci USA 82: 488-92(1985); Kunkel, Methods Enzymol 85: 2763-6 (1988)). Amino acid mutations can occur in nature, too. The polypeptide of the present invention includes those proteins having the amino acid sequences of the human C1958V1 or C1958V2 protein in which one or more amino acids are mutated, provided the resulting mutated polypeptides are functionally equivalent to the human C1958V1 or C1958V2 protein. The number of amino acids to be mutated in such a mutant is generally 10 amino acids or less, preferably 6 amino acids or less, and more preferably 3 amino acids or less.

Mutated or modified proteins, proteins having amino acid sequences modified by substituting, deleting, inserting, and/or adding one or more amino acid residues of a certain amino acid sequence, have been known to retain the original biological activity (Mark et al., Proc Natl Acad Sci USA 81: 5662-6 (1984); Zoller and Smith, Nucleic Acids Res 10:6487-500 (1982); Dalbadie-McFarland et al., Proc Natl Acad Sci USA 79: 6409-13 (1982)).

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a polypeptide to which one or more amino acids residues are added to the amino acid sequence of human C1958V1 or C1958V2 protein is a fusion protein containing the human C1958V1 or C1958V2 protein. Fusion proteins are, fusions of the human C1958V1 or C1958V2 protein and other peptides or proteins, and are included in the present invention. Fusion proteins can be made by techniques well known to a person skilled in the art, such as by linking the DNA encoding the human C1958V1 or C1958V2 protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides that are fused to the protein of the present invention include, for example, FLAG (Hopp et al., Biotechnology 6: 1204-10 (1988)), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, and the like. Examples of proteins that may be fused to a protein of the invention include GST (glutathione-S-transferase), Influenza agglutinin (HA), immunoglobulin constant region, β-galactosidase, MBP (maltose-binding protein), and such.

Fusion proteins can be prepared by fusing commercially available DNA, encoding the fusion peptides or proteins discussed above, with the DNA encoding the polypeptide of the present invention and expressing the fused DNA prepared.

An alternative method known in the art to isolate functionally equivalent polypeptides is, for example, the method using a hybridization technique (Sambrook et al., Molecular Cloning 2nd ed. 9.47-9.58, Cold Spring Harbor Lab. Press (1989)). One skilled in the art can readily isolate a DNA having high homology with a whole or part of the DNA sequence encoding the human C1958V1 or C1958V2 protein (i.e., SEQ ID NO: 1 or 3), and isolate functionally equivalent polypeptides to the human C1958V1 or C1958V2 protein from the isolated DNA. The polypeptides of the present invention include those that are encoded by DNA that hybridize with a whole or part of the DNA sequence encoding the human C1958V1 or C1958V2 protein and are functionally equivalent to the human C1958V1 or C1958V2 protein. These polypeptides include mammal homologues corresponding to the protein derived from human (for example, a polypeptide encoded by a monkey, rat, rabbit and bovine gene). In isolating a cDNA highly homologous to the DNA encoding the human C1958V1 or C1958V2 protein from animals, it is particularly preferable to use tissues from placenta, liver, thyroid, trachea or bone marrow.

The condition of hybridization for isolating a DNA encoding a polypeptide functionally equivalent to the human C1958V1 or C1958V2 protein can be routinely selected by a person skilled in the art. For example, hybridization may be performed by conducting prehybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringent condition is, for example, 42° C., 2×SSC, 0.1% SDS, or preferably 50° C., 2×SSC, 0.1% SDS. More preferably, high stringent conditions are used. A high stringent condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors, such as temperature and salt concentration, can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a polypeptide functionally equivalent to the human C1958V1 or C1958V2 protein, using a primer synthesized based on the sequence information of the protein encoding DNA (SEQ ID NO: 1 or 3).

Polypeptides that are functionally equivalent to the human C1958V1 or C1958V2 protein encoded by the DNA isolated through the above hybridization techniques or gene amplification techniques, normally have a high homology to the amino acid sequence of the human C1958V1 or C1958V2 protein. "High homology" typically refers to a homology of 40% or higher, preferably 60% or higher, more preferably 80% or higher, even more preferably 95% or higher. The homology of a polypeptide can be determined by following the algorithm in "Wilbur and Lipman, Proc Natl Acad Sci USA 80: 726-30 (1983)".

The polypeptides of the present invention can be prepared as recombinant proteins or natural proteins, by methods well known to those skilled in the art. A recombinant protein can be prepared by inserting a DNA, which encodes the polypeptide of the present invention (for example, the DNA comprising the nucleotide sequence of SEQ ID NO: 1 or 3), into an appropriate expression vector, introducing the vector into an appropriate host cell, obtaining the extract, and purifying the polypeptide by subjecting the extract to chromatography, for example, ion exchange chromatography, reverse phase chromatography, gel filtration, or affinity chromatography utilizing a column to which antibodies against the protein of the present invention is fixed, or by combining more than one of aforementioned columns.

Also when the polypeptide of the present invention is expressed within host cells (for example, animal cells and E. coli) as a fusion protein with glutathione-S-transferase protein or as a recombinant protein supplemented with multiple histidines, the expressed recombinant protein can be purified using a glutathione column or nickel column. Alternatively, when the polypeptide of the present invention is expressed as a protein tagged with c-myc, multiple histidines, or FLAG, it can be detected and purified using antibodies to c-myc, His, or FLAG, respectively.

After purifying the fusion protein, it is also possible to exclude regions other than the objective polypeptide by cutting with thrombin or factor-Xa as required.

A natural protein can be isolated by methods known to a person skilled in the art, for example, by contacting the affinity column, in which antibodies binding to the C1958V1 or C1958V2 protein described below are bound, with the extract of tissues or cells expressing the polypeptide of the present invention. The antibodies can be polyclonal antibodies or monoclonal antibodies.

The present invention also encompasses partial peptides of the polypeptide of the present invention. The partial peptide has an amino acid sequence specific to the polypeptide of the present invention and consists of at least 7 amino acids, preferably 8 amino acids or more, and more preferably 9 amino acids or more. The partial peptide can be used, for example, for preparing antibodies against the polypeptide of the present invention, screening for a compound that binds to the polypeptide of the present invention, and screening for inhibitors of the polypeptide of the present invention.

A partial peptide of the invention can be produced by genetic engineering, by known methods of peptide synthesis, or by digesting the polypeptide of the invention with an appropriate peptidase. For peptide synthesis, for example, solid phase synthesis or liquid phase synthesis may be used.

Furthermore, the present invention provides polynucleotides encoding the polypeptide of the present invention. The polynucleotides of the present invention can be used for the in vivo or in vitro production of the polypeptide of the present invention as described above, or can be applied to gene therapy for diseases attributed to genetic abnormality in the gene encoding the protein of the present invention. Any form of the polynucleotide of the present invention can be used so long as it encodes the polypeptide of the present invention, including mRNA, RNA, cDNA, genomic DNA, chemically synthesized polynucleotides. The polynucleotide of the present invention includes a DNA comprising a given nucleotide sequences as well as its degenerate sequences, so long as the resulting DNA encodes a polypeptide of the present invention.

The polynucleotide of the present invention can be prepared by methods known to a person skilled in the art. For example, the polynucleotide of the present invention can be prepared by: preparing a cDNA library from cells which express the polypeptide of the present invention, and conducting hybridization using a partial sequence of the DNA of the present invention (for example, SEQ ID NO: 1 or 3) as a probe. A cDNA library can be prepared, for example, by the method described in Sambrook et al., Molecular Cloning, Cold Spring Harbor Laboratory Press (1989); alternatively, commercially available cDNA libraries may be used. A cDNA library can be also prepared by: extracting RNAs from cells expressing the polypeptide of the present invention, synthesizing oligo DNAs based on the sequence of the DNA of the present invention (for example, SEQ ID NO: 1 or 3), conducting PCR using the oligo DNAs as primers, and amplifying cDNAs encoding the protein of the present invention.

In addition, by sequencing the nucleotides of the obtained cDNA, the translation region encoded by the cDNA can be routinely determined, and the amino acid sequence of the polypeptide of the present invention can be easily obtained. Moreover, by screening the genomic DNA library using the obtained cDNA or parts thereof as a probe, the genomic DNA can be isolated.

More specifically, mRNAs may first be prepared from a cell, tissue, or organ (e.g., placenta, liver, thyroid, trachea or bone marrow) in which the object polypeptide of the invention is expressed. Known methods can be used to isolate mRNAs; for instance, total RNA may be prepared by guanidine ultracentrifugation (Chirgwin et al., Biochemistry 18:5294-9 (1979)) or AGPC method (Chomczynski and Sacchi, Anal Biochem 162:156-9 (1987)). In addition, mRNA may be purified from total RNA using mRNA Purification Kit (Pharmacia) and such or, alternatively, mRNA may be directly purified by QuickPrep mRNA Purification Kit (Pharmacia).

The obtained mRNA is used to synthesize cDNA using reverse transcriptase. cDNA may be synthesized using a commercially available kit, such as the AMV Reverse Transcriptase First-strand cDNA Synthesis Kit (Seikagaku Kogyo). Alternatively, cDNA may be synthesized and amplified following the 5'-RACE method (Frohman et al., Proc Natl Acad Sci USA 85: 8998-9002 (1988); Belyavsky et al., Nucleic Acids Res 17: 2919-32 (1989)), which uses a primer and such, described herein, the 5'-Ampli FINDER RACE Kit (Clontech), and polymerase chain reaction (PCR).

A desired DNA fragment is prepared from the PCR products and ligated with a vector DNA. The recombinant vectors are used to transform E. coli and such, and a desired recombinant vector is prepared from a selected colony. The nucleotide sequence of the desired DNA can be verified by conventional methods, such as dideoxynucleotide chain termination.

The nucleotide sequence of a polynucleotide of the invention may be designed to be expressed more efficiently by taking into account the frequency of codon usage in the host to be used for expression (Grantham et al., Nucleic Acids Res 9: 43-74 (1981)). The sequence of the polynucleotide of the present invention may be altered by a commercially available kit or a conventional method. For instance, the sequence may be altered by digestion with restriction enzymes, insertion of a synthetic oligonucleotide or an appropriate polynucleotide fragment, addition of a linker, or insertion of the initiation codon (ATG) and/or the stop codon (TAA, TGA, or TAG).

Specifically, the polynucleotide of the present invention encompasses the DNA comprising the nucleotide sequence of SEQ ID NO: 1 or 3.

Furthermore, the present invention provides a polynucleotide that hybridizes under stringent conditions with a polynucleotide having a nucleotide sequence of SEQ ID NO: 1 or 3, and encodes a polypeptide functionally equivalent to the C1958V1 or C1958V2 protein of the invention described above. One skilled in the art may appropriately choose stringent conditions. For example, low stringent condition can be used. More preferably, high stringent condition can be used. These conditions are the same as that described above. The hybridizing DNA above is preferably a cDNA or a chromosomal DNA.

The present invention also provides a vector into which a polynucleotide of the present invention is inserted. A vector of the present invention is useful to keep a polynucleotide, especially a DNA, of the present invention in host cell, to express the polypeptide of the present invention.

When E. coli is a host cell and the vector is amplified and produced in a large amount in E. coli (e.g., JM109, DH5α, HB101, or XL1Blue), the vector should have "ori" to be amplified in E. coli and a marker gene for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc. can be used. In addition, pGEM-T, pDIRECT, and pT7 can also be used for subcloning and extracting cDNA as well as the vectors described above. When a vector is used to produce the protein of the present invention, an expression vector is especially useful. For example, an expression vector to be expressed in E. coli should have the above characteristics to be amplified in E. coli. When E. coli, such as JM109, DH5α, HB101, or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), or T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for polypeptide secretion. An exemplary signal sequence that directs the polypeptide to be secreted to the periplasm of the E. coli is the pelB signal sequence (Lei et al., J Bacteriol 169: 4379 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01), and expression vectors derived from *Bacillus subtilis* (e.g., pPL608, pKTH50) can be used for producing the polypeptide of the present invention.

In order to express the vector in animal cells, such as CHO, COS, or NIH3T3 cells, the vector should have a promoter necessary for expression in such cells, for example, the SV40 promoter (Mulligan et al., Nature 277: 108 (1979)), the MMLV-LTR promoter, the EF1α promoter (Mizushima et al., Nucleic Acids Res 18: 5322 (1990)), the CMV promoter, and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV, and pOP13.

In addition, methods may be used to express a gene stably and, at the same time, to amplify the copy number of the gene in cells. For example, a vector comprising the complementary DHFR gene (e.g., pCHO I) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transformed into COS cells comprising the SV40 T antigen expressing gene on the chromosome can be used.

A polypeptide of the present invention obtained as above may be isolated from inside or outside (such as medium) of host cells, and purified as a substantially pure homogeneous polypeptide. The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis. The method for polypeptide isolation and purification is not limited to any specific method; in fact, any standard method may be used.

For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by liquid chromatography, such as HPLC and FPLC. Thus, the present invention provides for highly purified polypeptides prepared by the above methods.

A polypeptide of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase, and so on.

The present invention provides an antibody that binds to the polypeptide of the invention. The antibody of the invention can be used in any form, such as monoclonal or polyclonal antibodies, and includes antiserum obtained by immunizing an animal such as a rabbit with the polypeptide of the invention, all classes of polyclonal and monoclonal antibodies, human antibodies, and humanized antibodies produced by genetic recombination.

A polypeptide of the invention used as an antigen to obtain an antibody may be derived from any animal species, but preferably is derived from a mammal such as a human, mouse, or rat, more preferably from a human. A human-derived polypeptide may be obtained from the nucleotide or amino acid sequences disclosed herein.

According to the present invention, the polypeptide to be used as an immunization antigen may be a complete protein or a partial peptide of the protein. A partial peptide may comprise, for example, the amino (N)-terminal or carboxy (C)-terminal fragment of a polypeptide of the present invention.

Herein, an antibody is defined as a protein that reacts with either the full length or a fragment of a polypeptide of the present invention.

A gene encoding a polypeptide of the invention or its fragment may be inserted into a known expression vector, which is then used to transform a host cell as described herein. The desired polypeptide or its fragment may be recovered from the outside or inside of host cells by any standard method, and may subsequently be used as an antigen. Alternatively, whole cells expressing the polypeptide or their lysates, or a chemically synthesized polypeptide may be used as the antigen.

Any mammalian animal may be immunized with the antigen, but preferably the compatibility with parental cells used for cell fusion is taken into account. In general, animals of Rodentia, Lagomorpha, or Primates are used. Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, sacred baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the polypeptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the polypeptide of the present invention using, for example, an affinity column coupled with the polypeptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes such as those infected by EB virus may be immunized with a polypeptide, polypeptide expressing cells, or their lysates in vitro. Then, the immunized lymphocytes are fused with human-derived myeloma cells that are capable of indefinitely dividing, such as U266, to yield a hybridoma producing a desired human antibody that is able to bind to the polypeptide can be obtained (Unexamined Published Japanese Patent Application No. (JP-A) Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography, or an affinity column to which the polypeptide of the present invention is coupled. The antibody of the present invention can be used not only for purification and detection of the polypeptide of the present invention, but also as a candidate for agonists and antagonists of the polypeptide of the present invention. In addition, this antibody can be applied to the antibody treatment for diseases related to the polypeptide of the present invention. When the obtained antibody is to be administered to the human body (antibody treatment), a human antibody or a humanized antibody is preferable for reducing immunogenicity.

For example, transgenic animals having a repertory of human antibody genes may be immunized with an antigen selected from a polypeptide, polypeptide expressing cells, or their lysates. Antibody producing cells are then collected from the animals and fused with myeloma cells to obtain hybridoma, from which human antibodies against the polypeptide can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the polypeptides of the invention. For instance, the antibody fragment may be Fab, $F(ab')_2$, Fv, or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region. Such antibodies can be prepared by using known technology.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS, and Sepharose F.F. (Pharmacia).

Exemplary chromatography, with the exception of affinity includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC, and FPLC.

For example, measurement of absorbance, enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, a polypeptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such asp-nitrophenyl phosphate, is added to the plate, and the absorbance is measured to evaluate the antigen binding activity of the sample. A fragment of the polypeptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the polypeptide of the invention, by exposing the antibody of the invention to a sample assumed to contain the polypeptide of the invention, and detecting or measuring the immune complex formed by the antibody and the polypeptide.

Because the method of detection or measurement of the polypeptide according to the invention can specifically detect or measure a polypeptide, the method may be useful in a variety of experiments in which the polypeptide is used.

The present invention also provides a polynucleotide which hybridizes with the polynucleotide encoding human C1958V1 or C1958V2 protein (SEQ ID NO: 1 or 3) or the complementary strand thereof, and which comprises at least 15 nucleotides. The polynucleotide of the present invention is preferably a polynucleotide which specifically hybridizes with the DNA encoding the polypeptide of the present invention. The term "specifically hybridize" as used herein, means that cross-hybridization does not occur significantly with DNA encoding other proteins, under the usual hybridizing conditions, preferably under stringent hybridizing conditions. Such polynucleotides include, probes, primers, nucleotides and nucleotide derivatives (for example, antisense oligonucleotides and ribozymes), which specifically hybridize with DNA encoding the polypeptide of the invention or its complementary strand. Moreover, such polynucleotide can be utilized for the preparation of DNA chip.

The present invention includes an antisense oligonucleotide that hybridizes with any site within the nucleotide sequence of SEQ ID NO: 1 or 3. This antisense oligonucleotide is preferably against at least 15 continuous nucleotides of the nucleotide sequence of SEQ ID NO: 1 or 3. The above-mentioned antisense oligonucleotide, which contains an initiation codon in the above-mentioned at least 15 continuous nucleotides, is even more preferred.

Derivatives or modified products of antisense oligonucleotides can be used as antisense oligonucleotides. Examples of such modified products include lower alkyl phosphonate modifications such as methyl-phosphonate-type or ethyl-phosphonate-type, phosphorothioate modifications and phosphoroamidate modifications.

The term "antisense oligonucleotides" as used herein means, not only those in which the nucleotides corresponding to those constituting a specified region of a DNA or mRNA are entirely complementary, but also those having a mismatch of one or more nucleotides, as long as the DNA or mRNA and the antisense oligonucleotide can specifically hybridize with the nucleotide sequence of SEQ ID NO: 1 or 3.

Such polynucleotides are contained as those having, in the "at least 15 continuous nucleotide sequence region", a homology of at least 70% or higher, preferably at 80% or higher, more preferably 90% or higher, even more preferably 95% or higher. The algorithm stated herein can be used to determine the homology. Such polynucleotides are useful as probes for the isolation or detection of DNA encoding the polypeptide of the invention as stated in a later example or as a primer used for amplifications.

The antisense oligonucleotide derivatives of the present invention act upon cells producing the polypeptide of the invention by binding to the DNA or mRNA encoding the polypeptide, inhibiting its transcription or translation, promoting the degradation of the mRNA, and inhibiting the expression of the polypeptide of the invention, thereby resulting in the inhibition of the polypeptide's function.

An antisense oligonucleotide derivative of the present invention can be made into an external preparation, such as a liniment or a poultice, by mixing with a suitable base material which is inactive against the derivatives.

Also, as needed, the derivatives can be formulated into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following usual methods.

The antisense oligonucleotide derivative is given to the patient by directly applying onto the ailing site or by injecting into a blood vessel so that it will reach the site of ailment. An antisense-mounting medium can also be used to increase durability and membrane-permeability. Examples are, liposome, poly-L-lysine, lipid, cholesterol, lipofectin or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

The present invention also includes small interfering RNAs (siRNA) comprising a combination of a sense strand nucleic acid and an antisense strand nucleic acid of the nucleotide sequence of SEQ ID NO: 1 or 3. More specifically, such siRNA for suppressing the expression of C1958V1 include those whose sense strand comprises the nucleotide sequence of SEQ ID NO: 25, 26 or 28 as the target sequences. The term "siRNA" refers to a double stranded RNA molecule which prevents translation of a target mRNA. Standard techniques are used for introducing siRNA into cells, including those wherein DNA is used as the template to transcribe RNA. The siRNA comprises a sense nucleic acid sequence and an antisense nucleic acid sequence of the polynucleotide encoding human C1958V1 or C1958V2 protein (SEQ ID NO: 1 or 3). The siRNA is constructed such that a single transcript (double stranded RNA) has both the sense and complementary antisense sequences from the target gene, e.g., a hairpin.

The method is used to alter gene expression of a cell, i.e., up-regulate the expression of C1958V1 or C1958V2, e.g., as a result of malignant transformation of the cells. Binding of the siRNA to C1958V1 or C1958V2 transcript in the target cell results in a reduction of protein production by the cell. The length of the oligonucleotide is at least 10 nucleotides and may be as long as the naturally occurring the transcript. Preferably, the oligonucleotide is 19-25 nucleotides in length. Most preferably, the oligonucleotide is less than 75, 50, 25 nucleotides in length. Examples of C1958V1 siRNA oligonucleotides which inhibit the expression in mammalian cells include oligonucleotides containing any of SEQ ID NO: 25, 26 or 28 as the target sequences.

The nucleotide sequence of siRNAs may be designed using a siRNA design computer program available from the Ambion website (www.ambion.com/techlib/misc/siRNA_finder.html). Nucleotide sequences for the siRNA are selected by the computer program based on the following protocol:

Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl, et al. recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with the binding of the siRNA endonuclease complex.
2. Compare the potential target sites to the human genome database and eliminate from consideration any target sequences with significant homology to other coding sequences. The homology search can be performed using BLAST, which can be found on the NCBI server at: www.ncbi.nlm.nih.gov/BLAST/.
3. Select qualifying target sequences for synthesis. At Ambion, preferably several target sequences can be selected along the length of the gene for evaluation.

The antisense oligonucleotide or siRNA of the invention inhibit the expression of the polypeptide of the invention and is thereby useful for suppressing the biological activity of the polypeptide of the invention. Also, expression-inhibitors, comprising the antisense oligonucleotide or siRNA of the invention, are useful in the point that they can inhibit the biological activity of the polypeptide of the invention. Therefore, a composition comprising the antisense oligonucleotide or siRNA of the present invention is useful in treating a cell proliferative disease such as cancer.

Moreover, the present invention provides a method for diagnosing a cell proliferative disease using the expression level of the polypeptides of the present invention as a diagnostic marker.

This diagnosing method comprises the steps of: (a) detecting the expression level of the C1958V1 or C1958V2 gene of the present invention; and (b) relating an elevation of the expression level to the cell proliferative disease, such as cancer.

The expression levels of the the C1958V1 or C1958V2 gene in a particular specimen can be estimated by quantifying mRNA corresponding to or protein encoded by the C1958V1 or C1958V2 gene. Quantification methods for mRNA are known to those skilled in the art. For example, the levels of mRNAs corresponding to the C1958V1 or C1958V2 gene can be estimated by Northern blotting or RT-PCR. Since the full-length nucleotide sequences of the C1958V1 or C1958V2 genes are shown in SEQ ID NO: 1 or 3, anyone skilled in the art can design the nucleotide sequences for probes or primers to quantify the C1958V1 or C1958V2 gene.

Also the expression level of the C1958V1 or C1958V2 gene can be analyzed based on the activity or quantity of protein encoded by the gene. A method for determining the quantity of the C1958V1 or C1958V2 protein is shown in bellow. For example, immunoassay method is useful for the determination of the proteins in biological materials. Any biological materials can be used for the determination of the protein or it's activity. For example, blood sample is analyzed for estimation of the protein encoded by a serum marker. On the other hand, a suitable method can be selected for the determination of the activity of a protein encoded by the C1958V1 or C1958V2 gene according to the activity of each protein to be analyzed.

Expression levels of the C1958V1 or C1958V2 gene in a specimen (test sample) are estimated and compared with those in a normal sample. When such a comparison shows that the expression level of the target gene is higher than those in the normal sample, the subject is judged to be affected with a cell proliferative disease. The expression level of C1958V1 or C1958V2 gene in the specimens from the normal sample and subject may be determined at the same time. Alternatively, normal ranges of the expression levels can be determined by a statistical method based on the results obtained by analyzing the expression level of the gene in specimens previously collected from a control group. A result obtained by comparing the sample of a subject is compared with the normal range; when the result does not fall within the normal range, the subject is judged to be affected with the cell proliferative disease. In the present invention, the cell proliferative disease to be diagnosed is preferably cancer. More preferably, when the expression level of the C1958V1 or C1958V2 gene is estimated and compared with those in a normal sample, the cell proliferative disease to be diagnosed is pancreatic cancer.

In the present invention, a diagnostic agent for diagnosing cell proliferative disease, such as cancer including pancreatic cancers, is also provided. The diagnostic agent of the present invention comprises a compound that binds to a polynucleotide or a polypeptide of the present invention. Preferably, an oligonucleotide that hybridizes to the polynucleotide of the present invention, or an antibody that binds to the polypeptide of the present invention may be used as such a compound.

Moreover, the present invention provides a method of screening for a compound for treating a cell proliferative disease using the polypeptide of the present invention. An embodiment of this screening method comprises the steps of: (a) contacting a test compound with a polypeptide of the present invention, (b) detecting the binding activity between the polypeptide of the present invention and the test compound, and (c) selecting a compound that binds to the polypeptide of the present invention.

The polypeptide of the present invention to be used for screening may be a recombinant polypeptide or a protein derived from the nature, or a partial peptide thereof. Any test compound, for example, cell extracts, cell culture supernatant, products of fermenting microorganism, extracts from marine organism, plant extracts, purified or crude proteins, peptides, non-peptide compounds, synthetic micromolecular compounds and natural compounds, can be used. The polypeptide of the present invention to be contacted with a test compound can be, for example, a purified polypeptide, a soluble protein, a form bound to a carrier, or a fusion protein fused with other polypeptides.

As a method of screening for proteins, for example, that bind to the polypeptide of the present invention using the polypeptide of the present invention, many methods well known by a person skilled in the art can be used. Such a screening can be conducted by, for example, immunoprecipitation method, specifically, in the following manner. The gene encoding the polypeptide of the present invention is expressed in animal cells and so on by inserting the gene to an expression vector for foreign genes, such as pSV2neo, pcDNA I, and pCD8. The promoter to be used for the expression may be any promoter that can be used commonly and include, for example, the SV40 early promoter (Rigby in Williamson (ed.), Genetic Engineering, vol. 3. Academic Press, London, 83-141 (1982)), the EF-1α promoter (Kim et al., Gene 91: 217-23 (1990)), the CAG promoter (Niwa et al., Gene 108: 193-200 (1991)), the RSV LTR promoter (Cullen, Methods in Enzymology 152: 684-704 (1987)) the SRα promoter (Takebe et al., Mol Cell Biol 8: 466 (1988)), the CMV immediate early promoter (Seed and Aruffo, Proc Natl Acad Sci USA 84: 3365-9 (1987)), the SV40 late promoter (Gheysen and Fiers, J Mol Appl Genet 1: 385-94 (1982)), the Adenovirus late promoter (Kaufman et al., Mol Cell Biol 9: 946 (1989)), the HSV TK promoter, and so on. The introduction of the gene into animal cells to express a foreign gene can be performed according to any methods, for example, the electroporation method (Chu et al., Nucleic Acids Res 15: 1311-26 (1987)), the calcium phosphate method (Chen and Okayama, Mol Cell Biol 7: 2745-52 (1987)), the DEAE dextran method (Lopata et al., Nucleic Acids Res 12: 5707-17 (1984); Sussman and Milman, Mol Cell Biol 4: 1642-3 (1985)), the Lipofectin method (Derijard, B Cell 7: 1025-37 (1994); Lamb et al., Nature Genetics 5: 22-30 (1993): Rabindran et al., Science 259: 230-4 (1993)), and so on. The polypeptide of the present invention can be expressed as a fusion protein comprising a recognition site (epitope) of a monoclonal antibody by introducing the epitope of the monoclonal antibody, whose specificity has been revealed, to the N- or C-terminus of the polypeptide of the present invention. A commercially available epitope-antibody system can be used (Experimental Medicine 13: 85-90 (1995)). Vectors which can express a fusion protein with, for example, β-galactosidase, maltose binding protein, glutathione S-transferase, green florescence protein (GFP) and so on by the use of its multiple cloning sites are commercially available.

A fusion protein prepared by introducing only small epitopes consisting of several to a dozen amino acids so as not to change the property of the polypeptide of the present invention by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage), and such, and monoclonal antibodies recognizing them can be used as the epitope-antibody system for screening proteins binding to the polypeptide of the present invention (Experimental Medicine 13: 85-90 (1995)).

In immunoprecipation, an immune complex is formed by adding these antibodies to cell lysate prepared using an appropriate detergent. The immune complex consists of the polypeptide of the present invention, a polypeptide comprising the binding ability with the polypeptide, and an antibody. Immunoprecipitation can be also conducted using antibodies against the polypeptide of the present invention, besides using antibodies against the above epitopes, which antibodies can be prepared as described above.

An immune complex can be precipitated, for example by Protein A sepharose or Protein G sepharose when the antibody is a mouse IgG antibody. If the polypeptide of the present invention is prepared as a fusion protein with an epitope, such as GST, an immune complex can be formed in the same manner as in the use of the antibody against the polypeptide of the present invention, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the polypeptide of the present invention is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of a protein has been revealed.

As a method for screening proteins binding to the polypeptide of the present invention using the polypeptide, for example, West-Western blotting analysis (Skolnik et al., Cell 65: 83-90 (1991)) can be used. Specifically, a protein binding to the polypeptide of the present invention can be obtained by preparing a cDNA library from cells, tissues, organs (for example, placenta, liver, thyroid, trachea or bone marrow), or cultured cells expected to express a protein binding to the polypeptide of the present invention using a phage vector (e.g., ZAP), expressing the protein on LB-agarose, fixing the protein expressed on a filter, reacting the purified and labeled polypeptide of the present invention with the above filter, and detecting the plaques expressing proteins bound to the polypeptide of the present invention according to the label. The polypeptide of the invention may be labeled by utilizing the binding between biotin and avidin, or by utilizing an antibody that specifically binds to the polypeptide of the present invention, or a peptide or polypeptide (for example, GST) that is fused to the polypeptide of the present invention. Methods using radioisotope or fluorescence and such may be also used.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet 10: 286-92 (1994)").

In the two-hybrid system, the polypeptide of the invention is fused to the SRF-binding region or GAL4-binding region and expressed in yeast cells. A cDNA library is prepared from cells expected to express a protein binding to the polypeptide of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to E. coli and expressing the protein.

As a reporter gene, for example, Ade2 gene, lacZ gene, CAT gene, luciferase gene and such can be used in addition to the HIS3 gene.

A compound binding to the polypeptide of the present invention can also be screened using affinity chromatography. For example, the polypeptide of the invention may be immobilized on a carrier of an affinity column, and a test compound, containing a protein capable of binding to the polypeptide of the invention, is applied to the column. A test compound herein may be, for example, cell extracts, cell lysates, etc. After loading the test compound, the column is washed, and compounds bound to the polypeptide of the invention can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the polypeptide of the invention and a test compound can be observed real-time as a surface plasmon resonance signal, using only a minute amount of polypeptide and without labeling (for example, BIAcore, Pharmacia). Therefore, it is possible to evaluate the binding between the polypeptide of the invention and a test compound using a biosensor such as BIAcore.

The methods of screening for molecules that bind when the immobilized polypeptide of the present invention is exposed to synthetic chemical compounds, or natural substance banks, or a random phage peptide display library, and the methods of screening using high-throughput based on combinatorial chemistry techniques (Wrighton et al., Science 273: 458-64 (1996); Verdine, Nature 384: 11-13 (1996); Hogan, Nature 384: 17-9 (1996)) to isolate not only proteins but chemical compounds that bind to the protein of the present invention (including agonist and antagonist) are well known to one skilled in the art.

Alternatively, the screening method of the present invention may comprise the following steps:

a) contacting a candidate compound with a cell into which a vector comprising the transcriptional regulatory region of one or more marker genes and a reporter gene that is expressed under the control of the transcriptional regulatory region has been introduced, wherein the one or more marker genes are selected from the group consisting of C1958V1 or C1958V2, b) measuring the activity of said reporter gene; and c) selecting a compound that reduces the expression level of said reporter gene as compared to a control.

Suitable reporter genes and host cells are well known in the art. The reporter construct required for the screening can be prepared by using the transcriptional regulatory region of a marker gene. When the transcriptional regulatory region of a marker gene has been known to those skilled in the art, a reporter construct can be prepared by using the previous sequence information. When the transcriptional regulatory region of a marker gene remains unidentified, a nucleotide segment containing the transcriptional regulatory region can be isolated from a genome library based on the nucleotide sequence information of the marker gene.

A compound isolated by the screening is a candidate for drugs which inhibit the activity of the polypeptide of the present invention, for treating or preventing diseases attributed to, for example, cell proliferative diseases, such as cancer. A compound in which a part of the structure of the compound obtained by the present screening method having the activity of binding to the polypeptide of the present invention is converted by addition, deletion and/or replacement, is included in the compounds obtained by the screening method of the present invention.

In a further embodiment, the present invention provides methods for screening candidate agents which are potential targets in the treatment of cell proliferative disease. As discussed in detail above, by controlling the expression levels of C1958V1 or C1958V2, one can control the onset and progression of pancreatic cancer. Thus, candidate agents, which are potential targets in the treatment of cell proliferative disease, can be identified through screenings that use the expression levels and activities of C1958V1 or C1958V2 as indices. In the context of the present invention, such screening may comprise, for example, the following steps:

a) contacting a candidate compound with a cell expressing the C1958V1 or C1958V2; and b) selecting a compound that reduces the expression level of C1958V1 or C1958V2 in comparison with the expression level detected in the absence of the test compound.

Cells expressing at least one of C1958V1 or C1958V2 include, for example, cell lines established from pancreatic cancers; such cells can be used for the above screening of the present invention. The expression level can be estimated by methods well known to one skilled in the art. In the method of screening, a compound that reduces the expression level of at least one of C1958V1 or C1958V2 can be selected as candidate agents.

In another embodiment of the method for screening a compound for treating a cell proliferative disease of the present invention, the method utilizes biological activity of the polypeptide of the present invention as an index. Since the C1958V1 or C1958V2 proteins of the present invention have the activity of promoting cell proliferation, a compound which promotes or inhibits this activity of one of these proteins of the present invention can be screened using this activity as an index. This screening method includes the steps of: (a) contacting a test compound with the polypeptide of the present invention; (b) detecting the biological activity of the polypeptide of step (a); and (c) selecting a compound that suppresses the biological activity of the polypeptide in comparison with the biological activity detected in the absence of the test compound.

Any polypeptides can be used for screening so long as they comprise the biological activity of the C1958V1 or C1958V2 protein. Such biological activity includes cell-proliferating activity of the human C1958V1 or C1958V2 protein. For example, a human C1958V1 or C1958V2 protein can be used and polypeptides functionally equivalent to these proteins can also be used. Such polypeptides may be expressed endogenously or exogenously by cells.

Any test compounds, for example, cell extracts, cell culture supernatant, products of fermenting microorganism, extracts of marine organism, plant extracts, purified or crude proteins, peptides, non-peptide compounds, synthetic micromolecular compounds, natural compounds, can be used.

The compound isolated by this screening is a candidate for antagonists of the polypeptide of the present invention. The term "antagonist" refers to molecules that inhibit the function of the polypeptide of the present invention by binding thereto. Moreover, a compound isolated by this screening is a candidate for compounds which inhibit the in vivo interaction of the polypeptide of the present invention with molecules (including DNAs and proteins).

When the biological activity to be detected in the present method is cell proliferation, it can be detected, for example, by preparing cells which express the polypeptide of the present invention, culturing the cells in the presence of a test compound, and determining the speed of cell proliferation, measuring the cell cycle and such, as well as by measuring the colony forming activity.

The compound isolated by the above screenings is a candidate for drugs which inhibit the activity of the polypeptide of the present invention and can be applied to the treatment of diseases associated with the polypeptide of the present invention, for example, cell proliferative diseases including cancer. More particularly, when the biological activity of C1958V1 or C1958V2 protein is used as the index, compounds screened by the present method serve as a candidate for drugs for the treatment of pancreatic cancer.

Moreover, compound in which a part of the structure of the compound inhibiting the activity of C1958V1 or C1958V2 protein is converted by addition, deletion and/or replacement are also included in the compounds obtainable by the screening method of the present invention.

When administrating the compound isolated by the methods of the invention as a pharmaceutical for humans and other mammals, such as mice, rats, guinea-pigs, rabbits, chicken, cats, dogs, sheep, pigs, cattle, monkeys, baboons, chimpanzees, for treating a cell proliferative disease (e.g., cancer) the isolated compound can be directly administered or can be formulated into a dosage form using known pharmaceutical preparation methods. For example, according to the need, the drugs can be taken orally, as sugarcoated tablets, capsules, elixirs and microcapsules, or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannnose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80™ and HCO-50.

Sesame oil or Soy-bean oil can be used as a oleaginous liquid and may be used in conjunction with benzyl benzoate or benzyl alcohol as a solubilizers and may be formulated with a buffer, such as phosphate buffer and sodium acetate buffer; a pain-killer, such as procaine hydrochloride; a stabilizer, such as benzyl alcohol, phenol; and an anti-oxidant. The prepared injection may be filled into a suitable ampule.

Methods well known to one skilled in the art may be used to administer the inventive pharmaceutical compound to patients, for example as intraarterial, intravenous, percutaneous injections and also as intranasal, transbronchial, intramuscular or oral administrations. The dosage and method of administration vary according to the body-weight and age of a patient and the administration method; however, one skilled in the art can routinely select them. If said compound is encodable by a DNA, the DNA can be inserted into a vector for gene therapy and the vector administered to perform the therapy. The dosage and method of administration vary according to the body-weight, age, and symptoms of a patient but one skilled in the art can select them suitably.

For example, although there are some differences according to the symptoms, the dose of a compound that binds with the polypeptide of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

Moreover, the present invention provides a method for treating or preventing a cell proliferative disease, such as cancer, using an antibody against the polypeptide of the present invention. According to the method, a pharmaceutically effective amount of an antibody against the polypeptide of the present invention is administered. Since the expression of the C1958V1 or C1958V2 protein are up-regulated in cancer cells, and the suppression of the expression of these proteins leads to the decrease in cell proliferating activity, it is expected that cell proliferative diseases can be treated or prevented by binding the antibody and these proteins. Thus, an antibody against the polypeptide of the present invention are administered at a dosage sufficient to reduce the activity of the protein of the present invention, which is in the range of 0.1 to about 250 mg/kg per day. The dose range for adult humans is generally from about 5 mg to about 17.5 g/day, preferably about 5 mg to about 10 g/day, and most preferably about 100 mg to about 3 g/day.

Alternatively, an antibody binding to a cell surface marker specific for tumor cells can be used as a tool for drug delivery. For example, the antibody conjugated with a cytotoxic agent is administered at a dosage sufficient to injure tumor cells.

The present invention also relates to a method of inducing anti-tumor immunity comprising the step of administering C1958V1 or C1958V2 protein or an immunologically active fragment thereof, or a polynucleotide encoding the protein or fragments thereof. The C1958V1 or C1958V2 protein or the immunologically active fragments thereof are useful as vaccines against cell proliferative diseases. In some cases the proteins or fragments thereof may be administered in a form bound to the T cell receptor (TCR) or presented by an antigen presenting cell (APC), such as macrophage, dendritic cell (DC), or B-cells. Due to the strong antigen presenting ability of DC, the use of DC is most preferable among the APCs. In the present invention, vaccine against cell proliferative disease refers to a substance that has the function to induce anti-tumor immunity upon inoculation into animals. According to the present invention, polypeptides encoded by SEQ ID NO: 1 or 3 were suggested to be HLA-A24 or HLA-A*0201 restricted epitopes peptides that may induce potent and specific immune response against pancreatic cancer cells expressing C1958V1 or C1958V2. In general, anti-tumor immunity includes immune responses such as follows:

induction of cytotoxic lymphocytes against tumors,
induction of antibodies that recognize tumors, and
induction of anti-tumor cytokine production.

Therefore, when a certain protein induces any one of these immune responses upon inoculation into an animal, the protein is decided to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to T cell by APC, and detecting the induction of CTL. Furthermore, APC has the effect of activating CD4+ T cells, CD8+ T cells, macrophages, eosinophils, and NK cells. Since CD4+ T cells and CD8+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC, and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, the method of evaluating the degree of tumor cell damage using $^3$H-thymidine uptake activity or LDH (lactose dehydrogenase)-release as the indicator is also well known.

Apart from DC, peripheral blood mononuclear cells (PBMCs) may also be used as the APC. The induction of CTL is reported that the it can be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against tumors. Furthermore, APC that acquired the ability to induce CTL against tumors by contacting with the polypeptides are useful as vaccines against tumors. Furthermore, CTL that acquired cytotoxicity due to presentation of the polypeptide antigens by APC can be also used as vaccines against tumors. Such therapeutic methods for tumors using anti-tumor immunity due to APC and CTL are referred to as cellular immunotherapy.

Generally, when using a polypeptide for cellular immunotherapy, efficiency of the CTL-induction is known to increase by combining a plurality of polypeptides having different structures and contacting them with DC. Therefore, when stimulating DC with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by those antibodies, the polypeptide can be determined to have an ability to induce anti-tumor immunity.

Anti-tumor immunity is induced by administering the vaccine of this invention, and the induction of anti-tumor immunity enables treatment and prevention of cell proliferating diseases, such as pancreatic cancers. Therapy against cancer or prevention of the onset of cancer includes any of the steps, such as inhibition of the growth of cancerous cells, involution of cancer, and suppression of occurrence of cancer. Decrease in mortality of individuals having cancer, decrease of tumor markers in the blood, alleviation of detectable symptoms accompanying cancer, and such are also included in the therapy or prevention of cancer. Such therapeutic and preventive effects are preferably statistically significant. For example, in observation, at a significance level of 5% or less, wherein the therapeutic or preventive effect of a vaccine against cell proliferative diseases is compared to a control without vaccine administration. For example, Student's t-test, the Mann-Whitney U-test, or ANOVA may be used for statistical analyses.

The above-mentioned protein having immunological activity or a vector encoding the protein may be combined with an adjuvant. An adjuvant refers to a compound that enhances the immune response against the protein when administered together (or successively) with the protein having immunological activity. Examples of adjuvants include cholera toxin, *salmonella* toxin, alum, and such, but are not limited thereto. Furthermore, the vaccine of this invention may be combined appropriately with a pharmaceutically acceptable carrier. Examples of such carriers are sterilized water, physiological saline, phosphate buffer, culture fluid, and such. Furthermore, the vaccine may contain as necessary, stabilizers, suspensions, preservatives, surfactants, and such. The vaccine is administered systemically or locally. Vaccine administration may be performed by single administration, or boosted by multiple administrations.

When using APC or CTL as the vaccine of this invention, tumors can be treated or prevented, for example, by the ex vivo method. More specifically, PBMCs of the subject receiving treatment or prevention are collected, the cells are contacted with the polypeptide ex vivo, and following the induction of APC or CTL, the cells may be administered to the subject. APC can be also induced by introducing a vector encoding the polypeptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of tumors from other individuals.

Furthermore, a pharmaceutical composition for treating or preventing a cell proliferative disease, such as cancer, comprising a pharmaceutically effective amount of the polypeptide of the present invention is provided. The pharmaceutical composition may be used for raising anti tumor immunity. The normal expression of C1958V1 or C1958V2 mainly observed in the placenta and weakly observed in the liver, thyroid, trachea or bone marrow. Therefore, Suppression of C1958V1 or C1958V2 gene may not adversely affect other organs. Thus, the C1958V1 or C1958V2 polypeptides are preferable for treating cell proliferative disease, especially pancreatic cancer. In the present invention, the polypeptide or fragment thereof is administered at a dosage sufficient to induce anti-tumor immunity, which is in the range of 0.1 mg to 10 mg, preferably 0.3 mg to 5 mg, more preferably 0.8 mg to 1.5 mg. The administrations are repeated. For example, 1 mg of the peptide or fragment thereof may be administered 4 times in every two weeks for inducing the anti-tumor immunity.

The following examples are presented to illustrate the present invention and to assist one of ordinary skill in making and using the same. The examples are not intended in any way to otherwise limit the scope of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications, and publications cited herein are incorporated by reference.

BEST MODE FOR CARRYING OUT THE INVENTION

The present invention is illustrated in details by following Examples, but is not restricted to these Examples.

1. Materials and Methods (1) Cell Lines and Clinical Materials

Human-pancreatic cancer cell lines Capan-1, Capan-2, Panc-1, Aspc-1, and MIApaca-2, KLM-1 and PK59 were kindly provided by Dr. Jae-Gahb Park (Korean Cell Line Bank, Cancer Research Institute, Seoul National University College of Medicine, Korea). All cells were cultured in appropriate media; i.e. RPMI-1640 (Sigma, St. Louis, Mo.) for Capan-1, Capan-2, and Aspc-1; Dulbecco's modified Eagle's medium (Invitrogen, Carlsbad, Calif.) for MIApaca-2, Panc-1, COS7. Each medium was supplemented with 10% fetal bovine serum (Cansera) and 1% antibiotic/antimycotic solution (Sigma). Cells were maintained at 37° C. in an atmosphere of humidified air with 5% $CO_2$). Clinical samples (pancreatic cancer and normal pancreatic duct) were obtained from surgical specimens, concerning which all patients had given informed consent.

(2) Isolation of a Novel Human Gene Represented by Spot #C1958 on our cDNA Microarray Fabrication of the cDNA microarray slides has been described elsewhere (Ono et al., 2000). For each analysis of expression profiles, duplicate sets of slides containing 23,040 cDNA spots was prepared to reduce experimental fluctuation. Briefly, total RNAs were purified from each sample of laser-microdissected cells, and T7-based RNA amplification was carried out to obtain adequate quantities of RNA for microarray experiments. Aliquots of amplified RNA from pancreatic cancer cells and the normal pancreatic ductal cells were labeled by reverse transcription with Cy5-dCTP and Cy3-dCTP, respectively (Amersham Biosciences, Buckinghamshire, UK). Hybridization, washing, and detection were carried out as described previously (Ono et al., 2000). Among the genes that appeared to up-regulated in tumor cells, the inventors focused on one with in-house identification number C1958 because its expression ratio was greater than 5.0 in more than 50% of the informative pancreatic cancer cases.

(3) Northern-blot Analysis

Human multiple-tissue Northern blots (Clontech, Palo Alto, Calif.) were hybridized with an [$\alpha^{32}P$]-dCTP-labeled amplification product of C1958 prepared by RT-PCR (see below). Pre-hybridization, hybridization and washing were performed according to the supplier's recommendations. The blots were autoradiographed with intensifying screens at −80° C. for 10 days. Specific probes for exon 4 of C1958 were prepared by PCR using a specific primer set as follows; 5'-GTCCTGAAAGTCAAGCACCTG-3'(SEQ ID NO: 5) and 5'-GAAGTTCTTGTTGGTGCTTATGG-3' (SEQ ID NO: 6).

(4) Semi-quantitative RT-PCR Analysis

Total RNAs extracted from clinical samples of laser-microdissected cells were into 350 μl of RLT lysis buffer (QIAGEN, Hilden, Germany), and the extracted RNAs were treated for DNase I (Roche, Basel, Switzerland) in the presence of 1 unit of RNase inhibitor (TOYOBO, Osaka, Japan) to remove any contaminating genomic DNA. After DNase I treatment, the RNAs were purified with an RNeasy Mini Kit (QIAGEN) according to the manufacturer's recommendations. All of the DNase I-treated RNAs were subjected to T7-based RNA amplification. Total RNA was extracted from cultured cells using TRIzol Reagent (Invitrogen) according to the manufacturer's protocol. Each extracted RNA was treated with DNase I (Roche).

The amplified RNA or total RNA were reversely transcribed for single-stranded cDNAs using random primer (Roche) or oligo(dT)$_{16}$ primer with Superscript II reverse transcriptase (Roche). Appropriate dilutions of each single-stranded cDNA for subsequent PCR amplification was prepared by monitoring the tubulin, alpha 3 (TUBA3) as a quantitative control. The primer sequences were

```
5'-CTTGGGTCTGTAACAAAGCATTC-3'    (SEQ ID NO: 7)
and

5'-AAGGATTATGAGGAGGTTGGTGT-3'    (SEQ ID NO: 8)
for TUBA3;

5'-GTCCTGAAAGTCAAGCACCTG-3'     (SEQ ID NO: 9)
and

5'-GAAGTTCTTGTTGGTGCTTATGG-3'   (SEQ ID NO: 10)
for C1958.
```

All reactions involved initial denaturation at 94° C. for 2 min followed by 22 cycles (for TUBA3) or 28 cycles (for C1958) at 94° C. for 30 s, 58° C. for 30 s, and 72° C. for 1 min, on a GeneAmp PCR system 9700 (PE Applied Biosystems).

(5) Construction of Expression Vector

The entire coding sequence of C1958V1 cDNA was amplified by RT-PCR with primers C1958V1-forward (5'-CCG-GAATTCGACATGGGGCTTAAGATGTCC-3'(SEQ ID NO: 11)) and C1958V1-reverse (5'-CCGCTCGAGGGCT-TCTGGGTCGATTTCTCC-3' (SEQ ID NO: 12)). The product was inserted into the EcoRI and XhoI sites of pcDNA3.1 (+).myc.his (Invitrogen), which carriers a cytomegalovirus (CMV) promoter and a gene conferring neomycin resistance. The construct (pcDNA3.1(+)-C1958-myc-his) was confirmed by DNA sequencing.

(6) Immunocytochemical Staining

COS7 cells were transfected transiently with pcDNA3.1 (+)-C1958V1-myc-his using FuGENE 6 (Roche) according to the manufacturer's instructions, then fixed with PBS containing 4% paraformaldehyde for 15 min, then rendered permeable with PBS containing 0.1% Triton X-100 for 2.5 min at 4° C. Subsequently the cells were covered with 3% BSA in PBS for 12 h at 4° C. to block non-specific hybridization, and incubated with a mouse anti-myc antibody (Sigma) at 1:1000 dilution. After washing with PBS, cells were stained by a FITC-conjugated anti-mouse secondary antibody (Organon Teknika). Nuclei were counter-stained with 4',6'-diamidine-2'-phenylindole dihydrochloride (DAPI). Fluorescent images were obtained under an ECLIPSE E800 microscope (Nikon, Tokyo, Japan).

(7) Western Blot Analysis

COS7 cells were transfected transiently with pcDNA3.1 (+)-C1958-myc-his using FuGENE 6 (Roche) according to the manufacturer's instructions, then the cells were washed twice with PBS and harvested in lysis buffer (150 mM NaCl, 1% Triton X-100, 50 mM Tris-HCl pH 7.4, 1 mM DTT, and 1× complete Protease Inhibitor Cocktail (Boehringer)). After the cells were homogenized and centrifuged at 10,000×g for 30 min, the supernatant were standardized for protein concentration by the Bradford assay (Bio-Rad). Proteins were separated by 12% SDS-PAGE and immunoblotted with mouse anti-myc (SANTA CRUZ) antibody.

(8) Construction of psiU6X3.0

Since snRNA U6 gene was reported to be transcribed by RNA polymerase III, which produce the short transcripts with uridines at the 3' end, we amplified the genomic fragment of snRNA U6 gene containing its promoter region by PCR using a set of primers, 5'-GGGGATCAGCGTTTGAGTAA-3' (SEQ ID NO: 13), and 5'-TAGGCCCCACCTCCTTCTAT-3' (SEQ ID NO: 14) and human placental DNA as a template. The product was purified and cloned into pCR plasmid vector using a TA cloning kit according to the supplier's protocol (Invitrogen). The BamHI, XhoI fragment containing the snRNA U6 gene was purified and cloned into nucleotide 1257 to 56 fragment of pcDNA3.1(+) plasmid, which was amplified by PCR with a set of primer, 5'-TGCGGATCCAGAG-CAGATTGTACTGAGAGT-3' (SEQ ID NO: 15) and 5'-CTCTATCTC GAGTGAGGCGGAAAGAACCA-3' (SEQ ID NO: 16). The ligated DNA was used for a template of PCR with primers, 5'-TTTAAGCTTGAAGACTATTTT-TACATCAGGTTGTTTTTCT-3' (SEQ ID NO: 17) and 5'-TTTAAGCTTGAAGACACGGTGTTTCGTC-CTTTCCACA-3' (SEQ ID NO: 18). The product was digested with HindIII, which was subsequently self-ligated to produce psiU6BX3.0 vector plasmid. For the control, psiU6BX-EGFP was prepared by cloning double-stranded oligonucleotides of 5'-CACCGAAGCAGCACGACTTCT-TCTTCAAGAGAGAAGAAGTCGTGCTGCTTC-3' (SEQ ID NO: 19) and 5'-AAAAGAAGCAGCACGACTTCT-TCTCTCTTGAAGAAGAAGTCGTGCTGCTTC-3' (SEQ ID NO: 20) into the BbsI site in the psiU6BX3.0 vector.

(9) Gene Silencing Effect of C1958V1

Plasmids expressing siRNAs were prepared by cloning of double-stranded oligonucleotides into psiU6BX3.0 vector. The target sequences for C1958 are 5'-CGACAAGCAC-CTGGACGTG-3' (SEQ ID NO: 25), 5'-ATGTGTGTCAG-CAGCAGCA-3' (SEQ ID NO: 26), 5'-TCCAGCCTGTC-CACTTCCA-3' (SEQ ID NO: 27) and 5'-GTTGTTTTTACAGATACGGA-3'(SEQ ID NO: 28). Human pancreatic cells from lines, KLM-1 and PK59, were plated onto 10-cm dishes (KLM-1; 2.5×10$^5$ cells/dish, PK59; 5×10$^5$ cells/dish) and transfected with psiU6BX-EGFP, or psiU6BX-C1958V1 using FuGENE6 reagent according to the supplier's recommendations (Roche). Total RNA was extracted from the cells 7 days after the transfection, and then the knockdown effect of siRNAs was confirmed by semi-quantitative RT-PCR using specific primers for C1958V1 and for β-actin (ACTB) as an internal control; 5'-GTCCT-GAAAGTCAAGCACCTG-3' (SEQ ID NO: 21) and 5'-GAAGTTCTTGTTGGTGCTTATGG-3' (SEQ ID NO: 22) for C1958, 5'-CATCCACGAAACTACCTTCAACT-3' (SEQ ID NO: 23) and 5'-TCTCCTTA-GAGAGAAGTGGGGTG-3' (SEQ ID NO: 24) for ACTB. Moreover, transfectants expressing siRNAs using KLM-1 and PK59 cell lines were grown for 9 days in selective media containing 0.6 mg/ml of neomycin. After fixation with 4% paraformaldehyde, transfected cells were stained with Giemsa solution to assess colony formation. MTT assays were performed to quantify cell viability. After 7 days of culture in the neomycin-containing medium, MTT solution (3-(4,5-dimethylthiazol-2-yl)-2,5-diphenyl tetrazolium bromide) (Sigma) was added at a concentration of 0.5 mg/ml. Following incubation at 37° C. for 4 h, acid-SDS (0.01N HCl/10% SDS) was added; the suspension was mixed vigorously and then incubated overnight at 37° C. to dissolve the dark blue crystals. Absorbance at 570 nm was measured with a Microplate Reader 550 (BioRad).

2. Results (1) Identification of C1958 as an Up-regulated Gene in Pancreatic Cancer Cells When gene-expression profiles of cancer cells from 18 pancreatic cancer patients using a cDNA microarray representing 23,040 human genes (Nakamura et al., 2003) were analyzed, 265 genes that were commonly up-regulated in pancreatic cancer cells were identified. Among them, the present inventors focused on a gene with in-house code C1958, which corresponded to EST Hs. 40530 in the Uni-Gene database in NCBI www.ncbi.nlm.nih.gov/UniGene/). Expression of this gene was elevated in 7 of 9 pancreatic cancers with greater signal intensities than the cut-off value on the microarray in comparison with normal pancreatic ducts (FIG. 1(a)). Subsequent semi-quantitative RT-PCR analysis confirmed elevated expression in 10 of 12 pancreatic cancers, and 2 of 5 pancreatic cancer cell line compared with normal pancreatic ducts (FIG. 1(b)).

Figure 2:
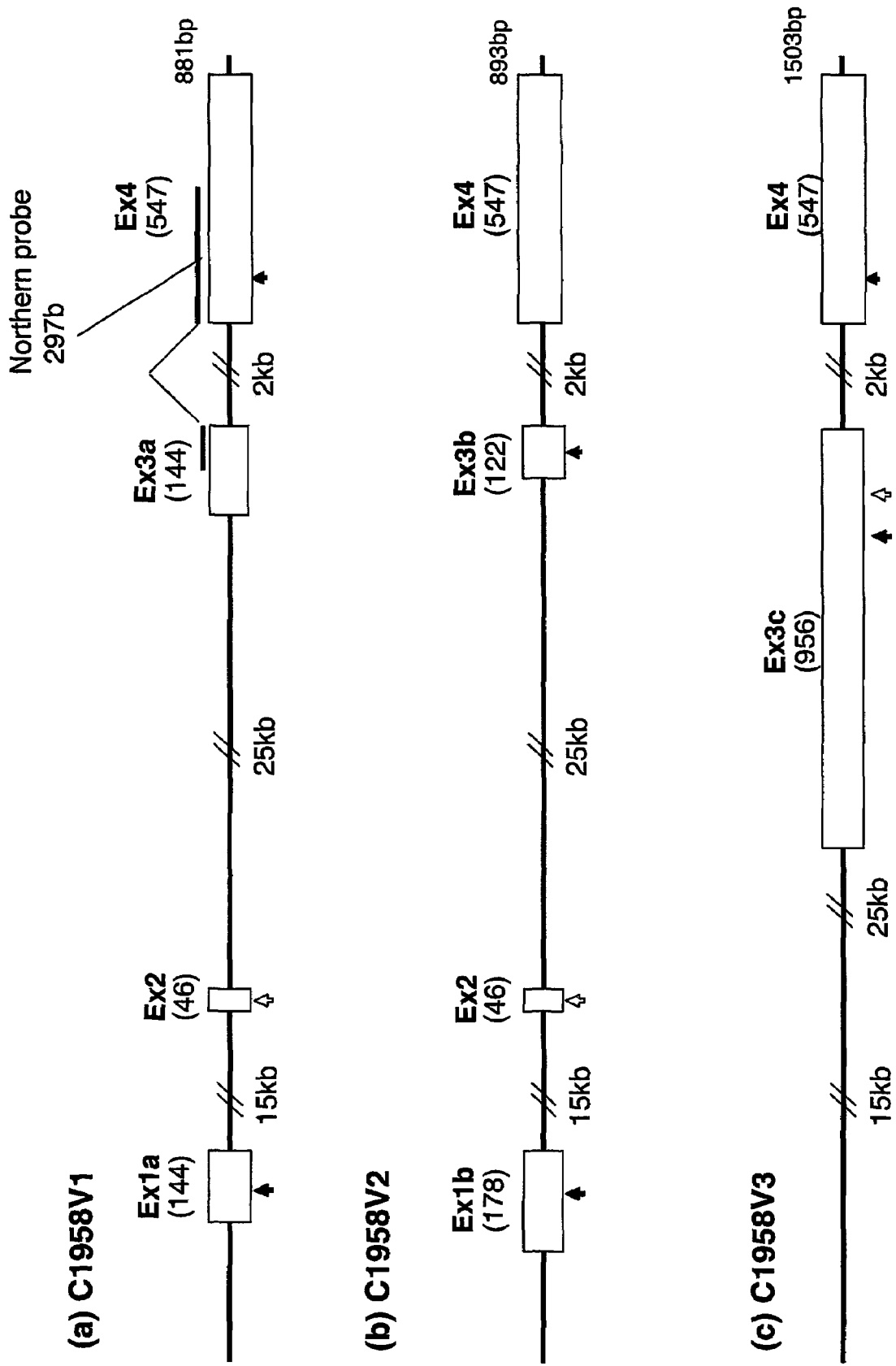
FIG. 2 depicts genomic structure of three different transcriptional variants of C1958. A black arrowhead indicates the stop codon and a blank arrowhead represents the initiation codon. The number in parenthesis shows length of each exon.

The C1958 gene was isolated by screening experiments using cDNA library prepared from pancreatic cancer cell line, Capan-1. There were three different transcriptional variants consisting of 4, 4 and 2 exons, (FIG. 2, (a) C1958V1 (Gen-Bank Accession number: AB115764), (b) C1958V2 (Gen-Bank Accession number: AB115765) and (c) C1958V3 (Gen-Bank Accession number: AB115766), respectively), located on the chromosome 16q spanning approximately 43 kb in the genome. There were variations among exon 1 and 3, and exon 2 was common to the C1958V1 and C1958V2, and exon 4 were also common to the all variants. Exon 1b of the C1958V2 variant was 34 bp longer than exon 1a of the C1958V1 at the 5' end, and exon 3b was 22 bp shorter than exon 3a of the C1958V1 at the 5' end, generating a novel stop codon within exon 3b. The full-length cDNA sequence of C1958V1 (SEQ ID NO: 1), C1958V2(SEQ ID NO: 3) variants contained 881 and 893 nucleotides, respectively. The ORF of the C1958V1 and C1958V2 start within exon 2, whereas the initiation site of translation was located within exon 3c of the C1958V3 variants, respectively.

Figure 3:
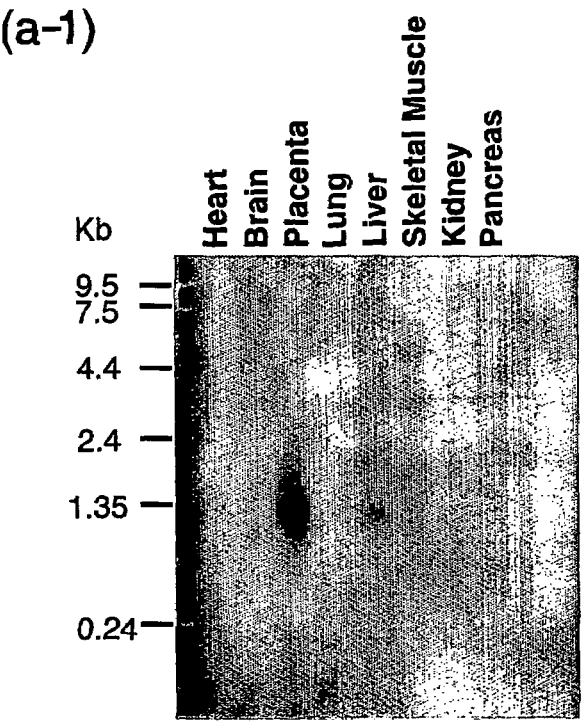
FIG. 3 depicts Northern blot analysis of the C1958 transcript in various human tissues (a-1,a-2,a-3) and pancreatic cancer cell lines (b). Molecular sizes are indicated at left.
Figure 3:
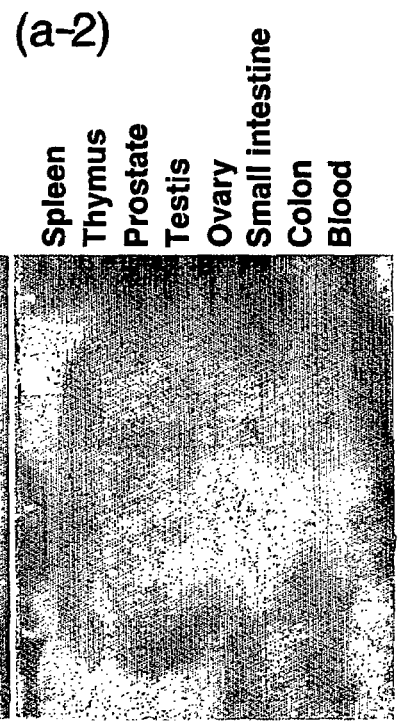
Figure 3:
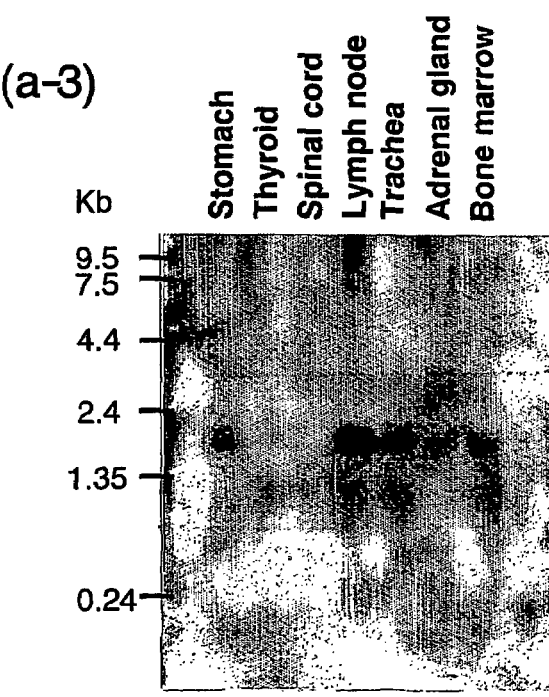
Figure 3:
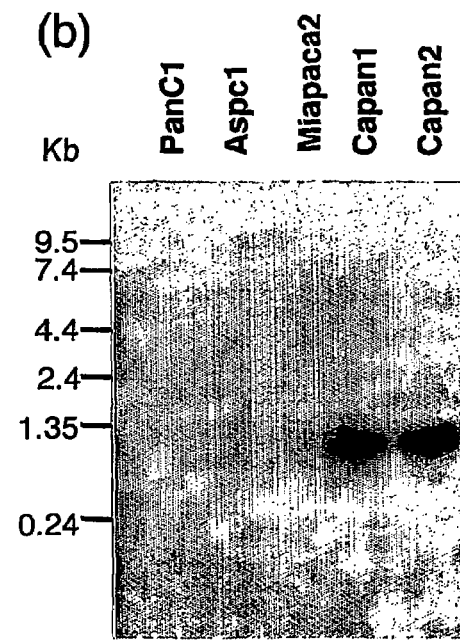

Northern analysis with a multiple-tissue blot using cDNA fragment C1958 as a probe (see Material and Method, and FIG. 2) revealed two transcript of approximately 1.8 kb and 1.2 kb (FIG. 3(a1-3)). The transcript of 1.8 kb was relatively higher expressed in lymph node, and was weakly expressed in stomach, trachea and bone marrow. On the other hand, the transcript of 1.2 kb was expressed abundantly in placenta and weakly in liver, thyroid, trachea and bone marrow. Moreover, Northern blot analysis with pancreatic cancer cell line blot using same probe revealed a transcript of approximately 1.2 kb (FIG. 3(b)).

Figure 4:
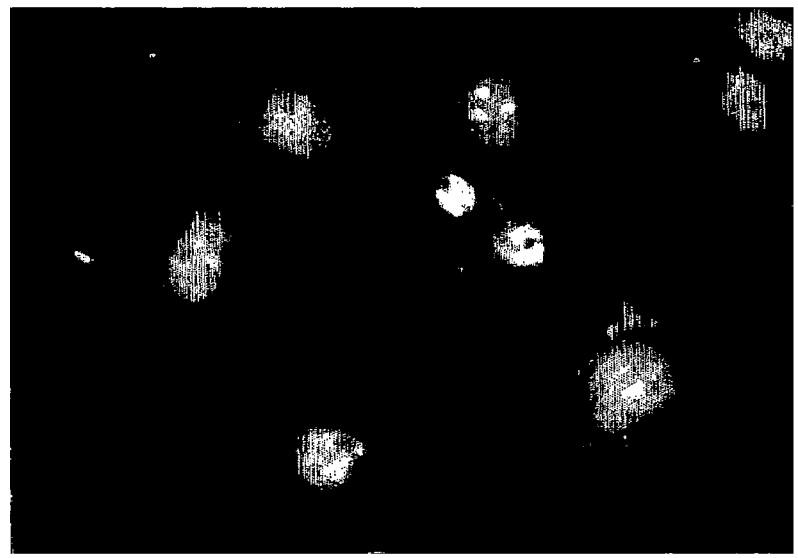
FIG. 4 (a) depicts subcellular localization of Myc-tagged C1958V1 in COS7 cells.
Figure 4:
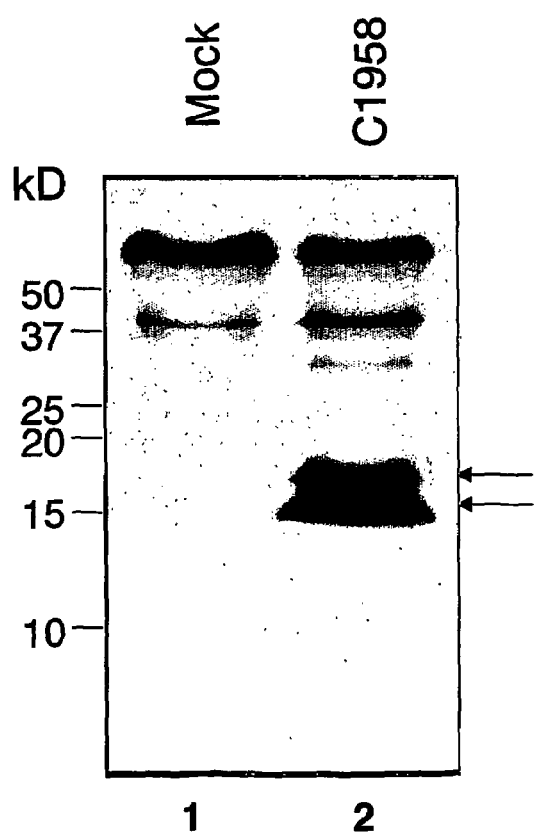

To investigate the sub-cellular localization of C1958V1 protein in mammalian cells, a plasmid expressing C1958V1 protein (pcDNA3.1(+)-C1958V1-myc-his) was transiently transfected into COS7 cells. As shown in FIG. 4(a), immunohistochemical staining reveals this C1958V1 product localized to the cytoplasmic apparatus in COS7 cells. Moreover, C1958V1 translated to gene products of a larger size than that predicted by Western blot analysis, suggesting this might be generated by posttranslational modification (FIG. 4(b)).

(2) Growth-inhibitory Effects of Small-interference RNA (siRNA) Designed to Reduce Expression of C1958

Figure 5:
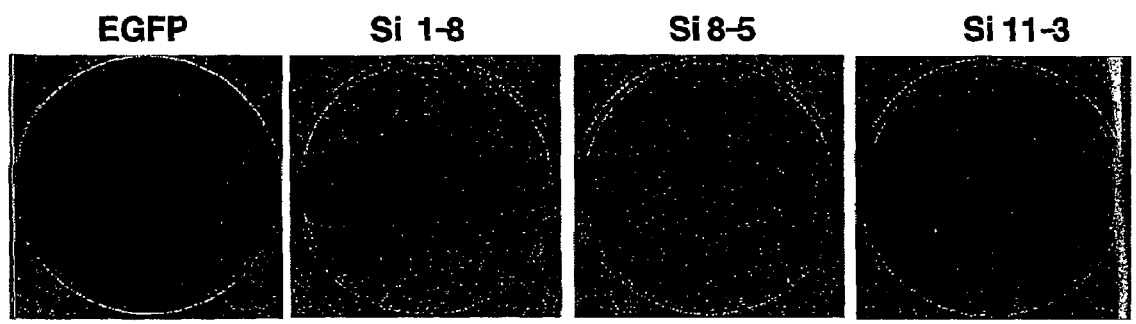
FIG. 5 depicts growth-inhibitory effects of small-interference RNAs (siRNAs) designed to reduce expression of C1958V1 in pancreatic cancer cells.
Figure 2:
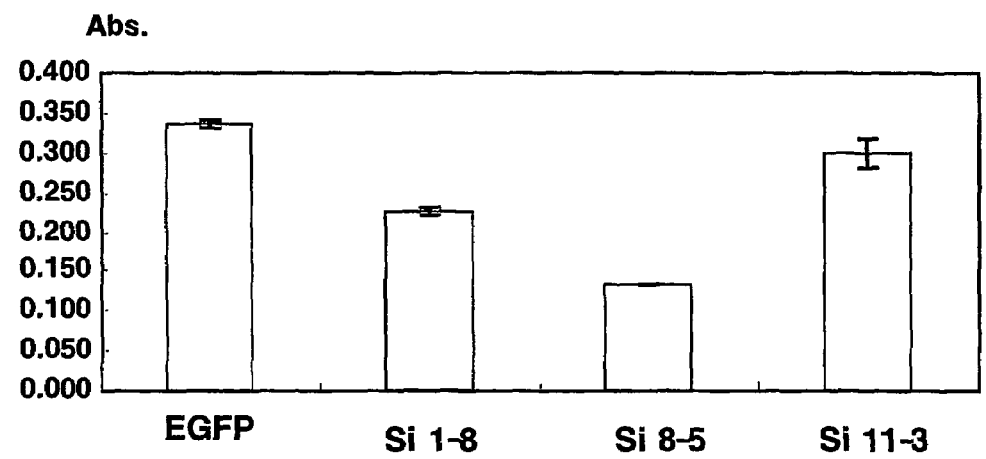

To assess the growth-promoting role of C1958V1, we knocked down the expression of endogenous C1958 in KLM-1 and PK59 cells, that are pancreatic cancer cell lines, by means of the mammalian vector-based RNA interference (RNAi) technique and examined the effect on cell growth (see Materials and Methods). As shown in FIG. 5(a), introduction of psiU6BX-C1958V1 (Si 8-5 and Si 11-3) clearly reduced expression of C1958V1 transcript in KLM-1 cell lines while no effect was observed in cells transfected with control plasmids (psiU6BX-EGFP siRNA expression vectors). To confirm the gene-specific growth reduction by psiU6BX-C1958V1, we performed colony-formation assays of the same two cell lines; as shown in FIGS. 5(b) and 5(d), introduction of psiU6BX-C1958V1 (Si 8-5) significantly suppressed growth of KLM-1 and PK59 cells, consisting with the result of above reduced expression, and psiU6BX-C1958V1 (Si 11-3) also moderately suppressed growth of both cell lines, and psiU6BX-C1958V1 (Si 1-8) also suppressed growth of PK59 cells. Moreover, MTT assays also indicated growth inhibition of KLM1 and/or PL59 cells when C1958V1 expression was repressed using psiU6BX-C1958V1 (Si 1-8, Si 8-5 and Si 11-3) (FIG. 5(c), 5(e)). Each result was verified by three independent experiments.

INDUSTRIAL APPLICABILITY

The expression of novel human genes C1958V1 or C1958V2 is markedly elevated in pancreatic cancer as compared to non-cancerous pancreatic tissues. Accordingly, these genes may serve as a diagnostic marker of cancer and the proteins encoded thereby may be used in diagnostic assays of cancer.

The present inventors have also shown that the cell growth is suppressed by antisense oligonucleotides or small interfering RNAs corresponding to the C1958V1 or C1958V2 gene. These findings suggest that each of C1958V1 or C1958V2 proteins stimulate oncogenic activity. Thus, each of these novel oncoproteins is useful targets for the development of anti-cancer pharmaceuticals. For example, agents that block the expression of C1958V1 or C1958V2, or prevent its activity may find therapeutic utility as anti-cancer agents, particularly anti-cancer agents for the treatment of pancreatic cancers. Examples of such agents include antisense oligonucleotides, small interfering RNAs, and antibodies that recognize C1958V1 or C1958V2.

While the invention has been described in detail and with reference to specific embodiments thereof, it will be apparent to one skilled in the art that various changes and modifications can be made therein without departing from the spirit and scope of the invention.

REFERENCES

Brentnall T A, Bronner M P, Byrd D R, Haggitt R C, and Kimmey M B. (1999). *Ann. Intern. Med*, 131, 247-255.

DiMagno E P, Reber H A and Tempero M A. (1999). *Gastroenterology*, 117, 1464-1484.

Greenlee R T, Hill-tHarmon M B, Murray T and Thun M. (2001). *CA. Cancer J. Clin.*, 51, 15-36.

Fujita M, Furukawa Y, Tsunoda T, Takana T, Ogawa M, and Nakamura Y. (2001). *Cancer Res.*, 61, 7722-7726.

Hao D and Rowinsky E K. (2002). *Cancer Invest.*, 20, 387-404.

Hasegawa S, Furukawa Y, Li M, Satoh S, Kato T, Watanabe T, Katagiri T, Tsunoda T, Yamaoka Y and Nakamura Y. (2002). *Cancer Res.*, 62, 7012-7017.

Ishiguro H, Tsunoda T, Tanaka T, Fujii Y, Nakamura Y and Furukawa Y (2001). *Oncogene*, 20, 5062-5066.

Ishiguro H, Shimokawa T, Tsunoda T, Tanaka, Fujii Y, Nakamura Y and Furukawa Y (2001). *Oncogene*, 21, 6387-6394.

Kaneta Y, Kagami Y, Katagiri T, Tsunoda T, Jin-nai I, Taguchi H, Hirai H, Ohnishi K, Ueda T, Emi N, Tomida A, Tsuruo T, Nakamura Y and Ohno R. (2002). *Jpn. J. Cancer Res.*, 93, 849-856.

Kaneta Y, Kagami Y, Tsunoda T, Ohno R. Nakamura Y and Katagiri T. (2003). *Int. J. Oncol.*, in press.

Kikuchi T, Daigo Y, Katagiri T, Tsunoda T, Okada K, Kakiuchi S, Zembutsu H, Furukawa Y, Kawamura M, Kobayashi K, Imai K and Nakamura Y. (2003) *Oncogene*, 22, 2192-2205.

Kitahara O, Katagiri T, Tsunoda T, Harima Y and Nakamura Y (2002). *Neoplasia*, 4, 295-303.

Klinkenbijl J H, Jeekel J, Sahmoud T, van Pel R, Couvreur M L, Veenhof C H, Arnaud J P, Gonzalez D G, de Wit L T, Hennipman A and Wils J. (1999). *Ann. Surg.*, 230, 776-782; discussion 782-784.

Laheru D, Biedrzycki B and Jaffee E M. (2001). *Cancer J.*, 7, 324-337.

Lin Y M, Ono K, Satoh S, Ishiguro H, Fujita M, Miwa N, Tanaka T, Tsunoda T, Yang K C, Nakamura Y and Furukawa Y. (2001). *Cancer Res.* 61, 6345-6349.

Lin Y M, Furukawa Y, Tsunoda T, Yue C T, Yang K C and Nakamura Y (2002). *Oncogene*, 21, 4120-4128.

Nagayama S, Katagiri T, Tsunoda T, Hosaka T, Nakashima Y, Araki N, Kusuzaki K, Nakayama T, Tsuboyama T, Nakamura T, Imamura M, Nakamura Y and Toguchida J. (2002). *Cancer Res.*, 62, 5859-5866.

Nakamura T, Furukawa Y, Nakagawa H, Tsunoda T, Ohigashi H, Murata K, Ishikawa O, Ohgaki K, Kashimura N, Miyamoto M, Hirano S, Kondo S, Katoh H, Nakamura Y, and Katagiri T. (2003) *Oncogene*, in press Okabe H, Satoh S, Kato T, Kitahara O, Yanagawa R, Yamaoka Y, Tsunoda T, Furukawa Y and Nakamura Y (2001). *Cancer Res.*, 61, 2129-2137.

Okutsu J, Tsunoda T, Kaneta Y, Katagiri T, Kitahara O, Zembutsu H, Yanagawa R, Miyawaki S, Kuriyama K, Kubota N, Kimura Y, Kubo K, Yagasaki F, Higa T, Taguchi H, Tobita T, Akiyama H, Takeshita A, Wang Y H, Motoji T, Ohno R and Nakamura Y (2002). *Mol. Cancer Ther.*, 1, 1035-1042.

Ono K, Tanaka T, Tsunoda T, Kitahara O, Kihara C, Okamoto A, Ochiai K, Takagiri T and Nakamura Y. (2000). *Cancer Res.*, 60, 5007-11.

Takahashi M, Fujita M, Furukawa Y, Hamamoto R, Shimokawa T, Miwa N, Ogawa M and Nakamura Y. (2002). *Cancer Res.*, 62, 5651-5656.

Rosenberg L. (2000). *Drugs*, 59, 1071-1089.

Yagyu R., Hamamoto R, Furukawa Y, Okabe H, Yamamura T and Nakamura Y. (2002). *Int. J. Oncol.*, 20, 1173-1178.

The invention claimed is:

1. An isolated polynucleotide comprising the nucleotide sequence of SEQ ID NO 1.

2. An isolated vector comprising the polynucleotide of claim 1.

3. An isolated host cell harboring the polynucleotide of claim 1 or a vector comprising the polynucleotide.

4. A composition comprising the polynucleotide of claim 1 as an active ingredient, and a pharmaceutically acceptable carrier.

5. The composition of claim 4, wherein the polynucleotide is incorporated into an expression vector.

* * * * *

UNITED STATES PATENT AND TRADEMARK OFFICE
CERTIFICATE OF CORRECTION

| | |
|---|---|
| PATENT NO. | : 7,601,826 B2 |
| APPLICATION NO. | : 10/529592 |
| DATED | : October 13, 2009 |
| INVENTOR(S) | : Nakamura et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 871 days.

Signed and Sealed this

Ninth Day of November, 2010

David J. Kappos
*Director of the United States Patent and Trademark Office*